(12) United States Patent
Watkins et al.

(10) Patent No.: US 8,741,946 B2
(45) Date of Patent: Jun. 3, 2014

(54) INHIBITORS OF FLAVIVIRIDAE VIRUSES

(75) Inventors: William J. Watkins, Saratoga, CA (US); Eda Canales, San Mateo, CA (US); Michael O'Neil Hanrahan Clarke, Redwood City, CA (US); Edward Doerffler, Union City, CA (US); Scott E. Lazerwith, San Francisco, CA (US)

(73) Assignee: Gilead Sciences, Inc., Foster City, CA (US)

(*) Notice: Subject to any disclaimer, the term of this patent is extended or adjusted under 35 U.S.C. 154(b) by 0 days.

(21) Appl. No.: 13/549,130

(22) Filed: Jul. 13, 2012

(65) Prior Publication Data

US 2013/0052161 A1 Feb. 28, 2013

Related U.S. Application Data

(60) Provisional application No. 61/507,544, filed on Jul. 13, 2011.

(51) Int. Cl.
*A61K 31/381* (2006.01)
*C07D 333/10* (2006.01)

(52) U.S. Cl.
USPC .............. 514/448; 549/29; 549/68; 549/69; 514/438; 514/447

(58) Field of Classification Search
USPC .............. 549/29, 68, 69; 514/438, 447, 448
See application file for complete search history.

(56) References Cited

U.S. PATENT DOCUMENTS

| | | | |
|---|---|---|---|
| 5,861,421 A | 1/1999 | Christensen, IV et al. |
| 6,881,741 B2 | 4/2005 | Chan et al. |
| 6,887,877 B2 | 5/2005 | Chan et al. |
| 7,402,608 B2 | 7/2008 | Chan et al. |
| 7,521,473 B2 | 4/2009 | Lee et al. |
| 7,569,600 B2 | 8/2009 | Denis et al. |
| 2002/0002199 A1 | 1/2002 | Jeppesen et al. |
| 2003/0229053 A1 | 12/2003 | Chan et al. |
| 2004/0116509 A1 | 6/2004 | Chan et al. |
| 2005/0119332 A1 | 6/2005 | Jeppesen et al. |
| 2006/0142347 A1 | 6/2006 | Chan et al. |
| 2006/0276533 A1 | 12/2006 | Denis et al. |
| 2007/0099929 A1 | 5/2007 | Thede et al. |
| 2008/0299080 A1 | 12/2008 | Chan et al. |
| 2009/0274655 A1 | 11/2009 | Grimes et al. |
| 2011/0020278 A1 | 1/2011 | Canales et al. |
| 2011/0178058 A1 | 7/2011 | Canales et al. |
| 2011/0178129 A1 | 7/2011 | Canales et al. |
| 2012/0156166 A1 | 6/2012 | Cho et al. |

FOREIGN PATENT DOCUMENTS

| | | |
|---|---|---|
| WO | WO-02/100846 | 12/2002 |
| WO | WO-02/100851 | 12/2002 |
| WO | WO-2004/052885 | 6/2004 |
| WO | WO-2005/095386 | 10/2005 |
| WO | WO 2006/072347 | 7/2006 |
| WO | WO 2006/072348 | 7/2006 |
| WO | WO-2007/093365 | 8/2007 |
| WO | WO-2008/058393 | 5/2008 |
| WO | WO-2010/065668 | 6/2010 |
| WO | WO-2011/011303 | 1/2011 |
| WO | WO-2011/031669 | 3/2011 |
| WO | WO-2011/068715 | 6/2011 |
| WO | WO-2011/088345 | 7/2011 |
| WO | WO-2012/006055 | 1/2012 |

OTHER PUBLICATIONS

Green et al (2012): STN International HCAPLUS database, Columbus (OH), accession No. 2012: 57086.*
U.S. Appl. No. 13/801,011, filed Mar. 13, 2013, Watkins et al.
U.S. Appl. No. 13/801,039, filed Mar. 13, 2013, Evans et al.
U.S. Appl. No. 13/800,991, filed Mar. 13, 2013, Hashash et al.
Boyer, N. et al. (2000) "Pathogenesis, Diagnosis and Management of Hepatitis C," *Journal of Hepatology* 32 (suppl 1):98-112.
Calisher, C. et al. (1989) "Antigenic Relationships between Flaviviruses as Determined by Cross-neutralization Tests with Polyclonal Antisera," *J. gen. Virol.* 70:37-43.
Di Bisceglie, A. et al. (1999) "Some 1.8 Percent of the U.S. Adult Population Are Infected with the Hepatitis C Virus, Most without Knowing It" *Scientific American* October pp. 80-85.
Domingo, E. et al. (1985) "The quasispecies (extremely heterogeneous) nature of viral RNA genome populations: biological relevance—a review" *Gene* 40:1-8.
Dymock, B. et al. (2000) "Novel approaches to the treatment of hepatitis C virus infection," *Antiviral Chemistry & Chemotherapy* 11(2):79-96.

(Continued)

*Primary Examiner* — Golam M M Shameem
(74) *Attorney, Agent, or Firm* — Kilpatrick Townsend & Stockton LLP

(57) ABSTRACT

Provided are compounds of Formula I:

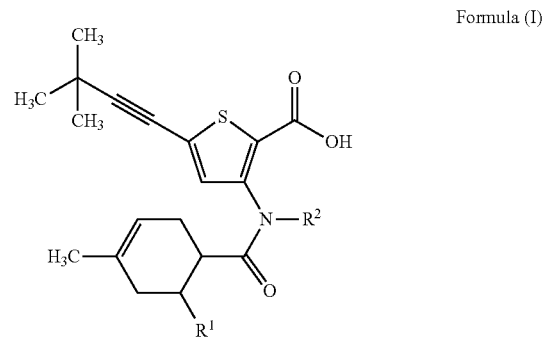

Formula (I)

and pharmaceutically acceptable salts and esters thereof. The compounds, compositions, and methods provided are useful for the treatment of Flaviviridae virus infections (e.g. hepatitis C infections), particularly drug resistant Flaviviridae virus infections.

11 Claims, No Drawings

(56) References Cited

OTHER PUBLICATIONS

Fukumoto, T. et al. (1996) "Viral Dynamics of Hepatitis C Early After Orthotopic Liver Transplantation: Evidence for Rapid Turnover of Serum Virions," *Hepatology* 24:1351-1354.

Gordon, C. et al. (2005) "Control of Hepatitis C: A Medicinal Chemistry Perspective," *Journal of Medicinal Chemistry* 48(1):1-20.

Herlihy, K. et al. (2008) "Development of Intergenotypic Chimeric Replicons to Determine the Broad-Spectrum Antiviral Activities of Hepatitis C Virus Polymerase Inhibitors," *Antimicrobial Agents and Chemotherapy* 52(10):3523-3531.

Maradpour, D. et al. (2007) "Replication of Hepatitis C Virus," *Nature Reviews Microbiology* 5(6):453-463.

Martell, M. et al. (1992) "Hepatitis C Virus (HCV) Circulates as a Population of Different but Closely Related Genomes: Quasispecies Nature of HCV Genome Distribution," *Journal of Virology* 66(5):3225-3229.

Moennig, V. et al. (1992) "The Pestiviruses," *Advances in Virus Research* 41:53-98.

Neumann, A. (1998) "Hepatitis C Viral Dynamics in Vivo and the Antiviral Efficacy of Interferon-α Therapy," *Science* 282:103-107.

Schul, W. (2007) "A Dengue Fever Viremia Model in Mice Shows Reduction in Viral Replication and Suppression of the Inflammatory Response after Treatment with Antiviral Drugs," *J. Infectious Disease* 195:665-674.

Scott, L. et al. (2002) "Interferon-α-2b Plus Ribavirin," *Drugs* 62:507-556.

International Search Report and Written Opinion mailed Sep. 29, 2010 for PCT/US2010/042394.

International Search Report and Written Opinion mailed May 2, 2011 for PCT/US2011/021279.

International Search Report and Written Opinion mailed Feb. 22, 2011 for PCT/US2011/021335.

International Search Report and Written Opinion mailed Nov. 15, 2010 for PCT/US2010/047983.

International Search Report and Written Opinion mailed Aug. 22, 2012 for PCT/US2012/046741.

Office Communications for U.S. Appl. No. 13/392,467.

Office Communications for U.S. Appl. No. 13/006,761.

Office Communications for U.S. Appl. No. 13/007,150.

Office Communications for U.S. Appl. No. 12/838,684.

PCT application No. PCT/US2012/046741, International Preliminary Report on Patentability, Date of Mailing Jan. 23, 2014, 7 pages.

* cited by examiner

INHIBITORS OF FLAVIVIRIDAE VIRUSES

PRIORITY OF INVENTION

This application claims priority to U.S. Provisional Patent Application No. 61/507,544 filed 13 Jul. 2011. The entire content of the provisional patent application is hereby incorporated herein by reference.

SEQUENCE LISTING

The instant application contains a Sequence Listing which has been submitted in ASCII format via EFS-Web and is hereby incorporated by reference in its entirety. Said ASCII copy, created on Nov. 1, 2012, is named 0457106651_SL.txt and is 4,096 bytes in size.

FIELD OF THE INVENTION

The present application includes novel inhibitors of Flaviviridae viruses, compositions containing such compounds, and therapeutic methods that include the administration of such compounds.

BACKGROUND OF THE INVENTION

The hepatitis C virus (HCV) is the leading cause of chronic liver disease worldwide (Boyer, N. et al. J Hepatol. 32:98-112, 2000) so a significant focus of current antiviral research is directed toward the development of improved methods of treatment of chronic HCV infections in humans (Di Bescegllie, A. M. and Bacon, B. R., Scientific American, October: 80-85, (1999); Gordon, C. P., et al., J. Med. Chem. 2005, 48, 1-20; Maradpour, D., et al., Nat. Rev. Micro. 2007, 5(6), 453-463). A number of HCV treatments are reviewed by Dymock et al. in Antiviral Chemistry & Chemotherapy, 11:2; 79-95 (2000). Virologic cures of patients with chronic HCV infection are difficult to achieve because of the prodigious amount of daily virus production in chronically infected patients and the high spontaneous mutability of HCV virus (Neumann, et al., Science 1998, 282, 103-7; Fukimoto, et al., Hepatology, 1996, 24, 1351-4; Domingo, et al., Gene, 1985, 40, 1-8; Martell, et al., J. Virol. 1992, 66, 3225-9).

Primarily two compounds, ribavirin, a nucleoside analog, and interferon-alpha (α) (IFN), have been used to treat chronic HCV infections in humans. Ribavirin alone is not effective in reducing viral RNA levels, has significant toxicity, and is known to induce anemia. The combination of IFN and ribavirin has been reported to be effective in the management of chronic hepatitis C (Scott, L. J., et al. Drugs 2002, 62, 507-556) but less than half the patients given this treatment show a persistent benefit. Recently, both telaprevir and boceprevir have also been approved in the United States for the treatment of HCV.

Additionally, alkynyl substituted thiophenes with anti-Flaviviridae virus activity have been disclosed by Chan, et al., WO 2008058393; Wunberg, et al., WO 2006072347; and Chan, et al., WO 2002100851; but none of these are currently approved as antiviral therapeutics. In spite of the above described reports, infections from the Flaviviridae virus family, including HCV, continue to cause significant mortality, morbidity and economic losses throughout the world. Therefore, there remains a need to develop effective treatments for Flaviviridae virus infections (e.g. HCV). In particular, there is a need for treatments for Flaviviridae virus infections that have developed resistance to one or more of the currently available therapies.

SUMMARY OF THE INVENTION

The invention provides compounds that are effective treatments for Flaviviridae virus infections. Additionally, certain compounds of the invention have useful activity against resistant Flaviviridae virus infections. Accordingly, in one aspect, provided is a compound of Formula I:

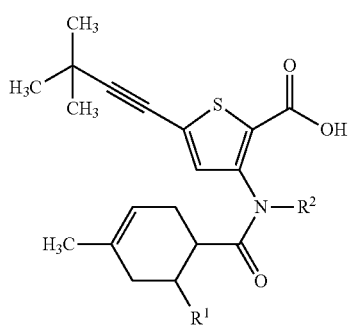

(I)

or a pharmaceutically acceptable salt or ester thereof, wherein:

$R^1$ is H or methyl; and $R^2$ is (C1-C12)alkyl, (C2-C12)alkenyl, (C2-C12)alkynyl, aryl, heterocycle, heteroaralkyl, or aralkyl.

In another aspect, a method for treating Flaviviridae viral infections is provided comprising administering a therapeutically effective amount of a compound of Formula I to a mammal in need thereof. The compound of Formula I is administered to a human subject in need thereof, such as a human being who is infected with viruses of the Flaviviridae family. In another embodiment, the compound of Formula I is administered to a human subject in need thereof, such as a human being who is infected with a HCV virus. In one embodiment, the treatment results in the reduction of one or more of the in viral loads or clearance of viral RNA in a patient.

In another embodiment, provided is a method of treating and/or preventing a disease caused by a viral infection wherein the viral infection is caused by a virus selected from the group consisting of dengue virus, yellow fever virus, West Nile virus, Japanese encephalitis virus, tick-borne encephalitis virus, Junjin virus, Murray Valley encephalitis virus, St Louis encephalitis virus, Omsk hemorrhagic fever virus, bovine viral disarrhea virus, Zika virus and Hepatitis C virus; by administering to a subject in need thereof a therapeutically effective amount of a compound of Formula I, or a pharmaceutically acceptable salt or ester thereof.

In another aspect, provided is the use of a compound of Formula I for the manufacture of a medicament for the treatment of Flaviviridae viral infections. In another aspect, provided is a compound of Formula I for use in treating a Flaviviridae viral infection. In one embodiment, the Flaviviridae viral infection is acute or chronic HCV infection. In one embodiment of each aspect of use and compound, the treatment results in the reduction of one or more of the viral loads or clearance of RNA in the patient.

In another aspect, provided is a method for treating or preventing HCV comprising administering an effective amount of a compound of Formula I to a patient in need thereof. In another aspect, provided is the use of a compound of the present invention for the manufacture of a medicament for the treatment or prevention of HCV.

In another aspect, provided is a use of a compound of Formula I for the treatment of a Flaviviridae viral infection or a Hepatitis C virus infection.

In another aspect, provided is a pharmaceutical composition comprising a compound of Formula I or a pharmaceutically acceptable salt or ester thereof and one or more pharmaceutically acceptable carriers or excipients. The pharmaceutical composition of Formula I may further comprise one or more additional therapeutic agents. The one or more additional therapeutic agent may be, without limitation, selected from: interferons, ribavirin or its analogs, HCV NS3 protease inhibitors, NS5A inhibitors, alpha-glucosidase 1 inhibitors, hepatoprotectants, mevalonate decarboxylase antagonists, antagonists of the renin-angiotensin system, other anti-fibrotic agents, endothelin antagonists, nucleoside or nucleotide inhibitors of HCV NS5B polymerase, non-nucleoside inhibitors of HCV NS5B polymerase, HCV NS4B inhibitors, inhibitors of viral entry and/or assembly, TLR-7 agonists, cyclophilin inhibitors, HCV IRES inhibitors, pharmacokinetic enhancers and other drugs for treating HCV; or mixtures thereof.

In another aspect, provided is a method for the treatment or prevention of the symptoms or effects of an HCV infection in an infected animal which comprises administering to, i.e. treating, said animal with a pharmaceutical combination composition or formulation comprising an effective amount of a Formula I compound, and a second compound having anti-HCV properties.

In another embodiment, provided are compounds of Formula I and pharmaceutically acceptable salts and esters thereof and all racemates, enantiomers, diastereomers, tautomers, polymorphs, pseudopolymorphs and amorphous forms thereof.

In another aspect, provided are processes and novel intermediates disclosed herein which are useful for preparing Formula I compounds.

In other aspects, novel methods for synthesis, analysis, separation, isolation, purification, characterization, and testing of the compounds of Formula I are provided.

The present invention includes combinations of aspects and embodiments, as well as preferences, as herein described throughout the present specification.

DETAILED DESCRIPTION

Reference will now be made in detail to certain embodiments of the invention, examples of which are illustrated in the accompanying structures and formulas. While the invention will be described in conjunction with the enumerated embodiments, it will be understood that they are not intended to limit the invention to those embodiments. On the contrary, the invention is intended to cover all alternatives, modifications, and equivalents, which may be included within the scope of the present invention as defined herein.

Each document referenced herein is incorporated by reference in its entirety for all purposes.

DEFINITIONS

Unless stated otherwise, the following terms and phrases as used herein are intended to have the following meanings. The fact that a particular term or phrase is not specifically defined should not be correlated to indefiniteness or lacking clarity, but rather terms herein are used within their ordinary meaning. When trade names are used herein, applicants intend to independently include the tradename product and the active pharmaceutical ingredient(s) of the tradename product.

The term "treating", and grammatical equivalents thereof, when used in the context of treating a disease, means slowing or stopping the progression of a disease, or ameliorating at least one symptom of a disease, more preferably ameliorating more than one symptom of a disease. For example, treatment of a hepatitis C virus infection can include reducing the HCV viral load in an HCV infected human being, and/or reducing the severity of jaundice present in an HCV infected human being.

As used in this application, the term "alkyl" represents a straight chain, branched chain or cyclic hydrocarbon moiety which may optionally be substituted by one or more of: halogen, nitro, nitroso, SO3R12, PO3RcRd, CONR13R14, C1-6 alkyl, C2-6 alkenyl, C2-6 alkynyl, C6-12 aralkyl, C6-12 aryl, C1-6 alkyloxy, C2-6 alkenyloxy, C2-6 alkynyloxy, C6-12 aryloxy, C(O)C1-6 alkyl, C(O)C2-6 alkenyl, C(O)C2-6 alkynyl, C(O)C6-12 aryl, C(O)C6-12 aralkyl, C3-10 heterocycle, hydroxyl, NR13R14, C(O)OR12, cyano, azido, amidino or guanido; wherein R12, Rc, Rd, R13 and R14 are each independently chosen from H, C1-12 alkyl, C2-12 alkenyl, C2-12 alkynyl, C6-14 aryl, C3-12 heterocycle, C3-18 heteroaralkyl, C6-18 aralkyl; or Rc and Rd are taken together with the oxygens to form a 5 to 10 membered heterocycle; or R13 and R14 are taken together with the nitrogen to form a 3 to 10 membered heterocycle. Useful examples of alkyls include isopropyl, ethyl, fluorohexyl or cyclopropyl. The term alkyl is also meant to include alkyls in which one or more hydrogen atoms is replaced by an oxygen, (e.g. a benzoyl) or an halogen, more preferably, the halogen is fluoro (e.g. CF3- or CF3CH2-). In one embodiment of the invention alkyl is a $(C_1-C_{12})$alkyl. In another embodiment of the invention alkyl is a $(C_1-C_6)$alkyl.

The terms "alkenyl" and "alkynyl" represent an alkyl containing at least one unsaturated group (e.g. allyl, acetylene, ethylene).

The term "aryl" represents a carbocyclic moiety containing at least one benzenoid-type ring which may optionally be substituted by one or more of halogen, nitro, nitroso, SO3R12, PO3RcRd, CONR13R14, C1-6 alkyl, C2-6 alkenyl, C2-6 alkynyl, C6-12 aralkyl, C6-12 aryl, C1-6 alkyloxy, C2-6 alkenyloxy, C2-6 alkynyloxy, C6-12 aryloxy, C(O)C1-6 alkyl, C(O)C2-6 alkenyl, C(O)C2-6 alkynyl, C(O)C6-12 aryl, C(O)C6-12 aralkyl, C3-10 heterocycle, hydroxyl, NR13R14, C(O)OR12, cyano, azido, amidino or guanido; wherein R12, Rc, Rd, R13 and R14 are each independently chosen from H, C1-12 alkyl, C2-12 alkenyl, C2-12 alkynyl, C6-14 aryl, C3-12 heterocycle, C3-18 heteroaralkyl, C6-18 aralkyl; or Rc and Rd are taken together with the oxygens to form a 5 to 10 membered heterocycle; or R13 and R14 are taken together with the nitrogen to form a 3 to 10 membered heterocycle. Examples of aryl include phenyl and naphthyl. In one embodiment of the invention the aryl carbocyclic moiety contains 6-14 carbon atoms. In another embodiment of the invention the aryl carbocyclic moiety contains 6-10 carbon atoms.

The term "aralkyl" represents an aryl group attached to the adjacent atom by a C1-6alkyl, C1-6alkenyl, or C1-6alkynyl (e.g., benzyl).

The term "heterocycle" represents a saturated or unsaturated, cyclic moiety wherein said cyclic moiety is interrupted by at least one heteroatom, (e.g. oxygen, sulfur or nitrogen) which may optionally be substituted halogen, nitro, nitroso, SO3R12, PO3RcRd, CONR13R14, C1-6 alkyl, C2-6 alkenyl, C2-6 alkynyl, C6-12 aralkyl, C6-12 aryl, C1-6 alkyloxy, C2-6 alkenyloxy, C2-6 alkynyloxy, C6-12 aryloxy, C(O)C1-6 alkyl, C(O)C2-6 alkenyl, C(O)C2-6 alkynyl, C(O)C6-12 aryl, C(O)C6-12 aralkyl, C3-10 heterocycle, hydroxyl, NR13R14, C(O)OR12, cyano, azido, amidino or guanido; wherein R12, Rc, Rd, R13 and R14 are each independently chosen from H, C1-12 alkyl, C2-12 alkenyl, C2-12 alkynyl, C6-14 aryl, C3-12 heterocycle, C3-18 heteroaralkyl, C6-18 aralkyl; or Rc and Rd are taken together with the oxygens to form a 5 to 10 membered heterocycle; or R13 and $R^{14}$ are taken together with the nitrogen to form a 3 to 10 membered heterocycle. It is understood that the term heterocyclic ring represents a mono or polycyclic (e.g., bicyclic) ring. Examples of heterocyclic rings include but are not limited to epoxide; furan; benzofuran; isobenzofuran; oxathiolane; dithiolane; dioxolane; pyrrole; pyrrolidine; imidazole; pyridine; pyrimidine; indole; piperidine; morpholine; thiophene and thiomorpholine. In one embodiment of the invention the heterocycle cyclic moiety contains 3-14 atoms. In another embodiment of the invention the heterocycle cyclic moiety contains 5-10 atoms.

The term "heteroaralkyl" represents an heterocycle group attached to the adjacent atom by a C1-6alkyl, C1-6 alkenyl, or C1-6alkynyl.

When there is a sulfur atom present, the sulfur atom can be at different oxidation levels, ie. S, SO, or SO2. All such oxidation levels are within the scope of the present invention.

In one embodiment of the invention the compound of formula (I) is a compound of formula (Ia) or I(b)

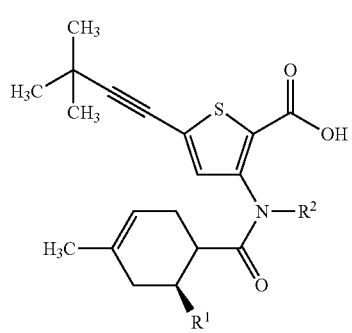

(Ia)

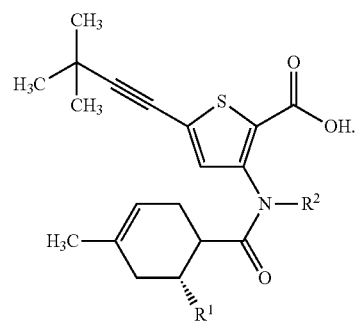

(Ib)

In one embodiment of the invention the compound of formula (I) is a compound of formula (Ic)-(If):

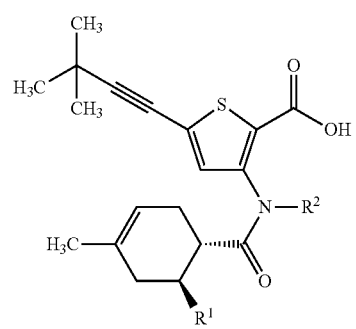

(Ic)

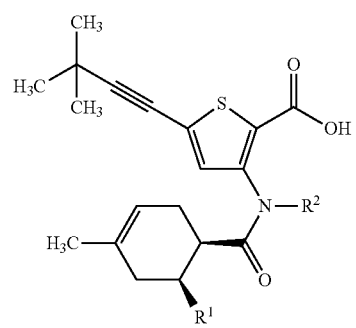

(Id)

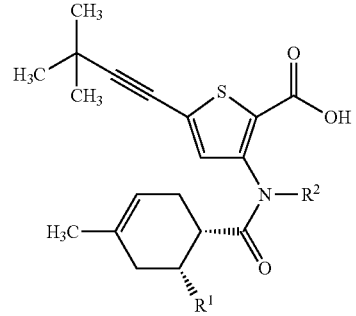

(Ie)

(If)
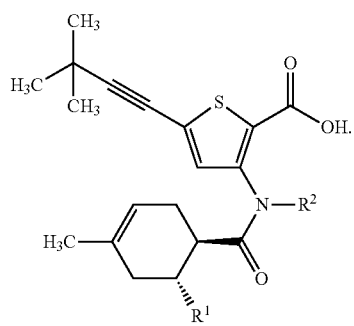
In one embodiment of the invention the compound of formula (I) is a compound of formula (Ig)-(Ip):
(Ig)
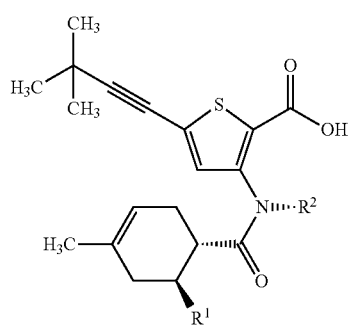
(Ih)
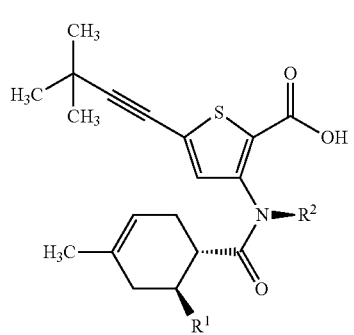
(Ii)
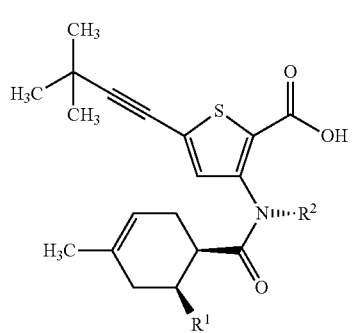
(Ij)
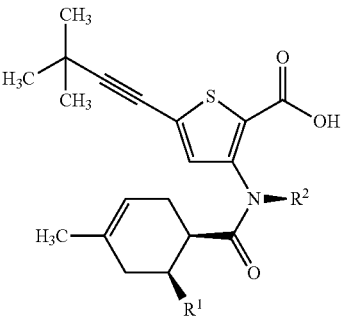
(Ik)
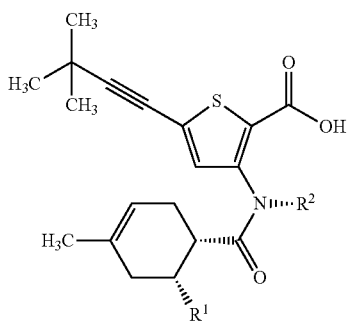
(Im)
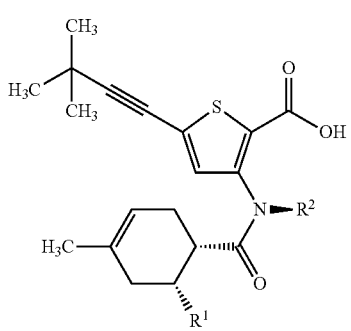
(In)
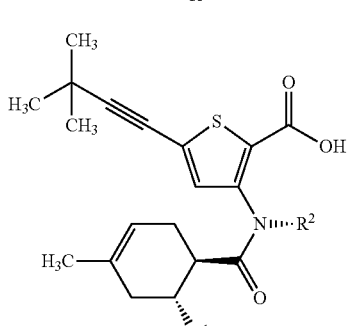
(Ip)
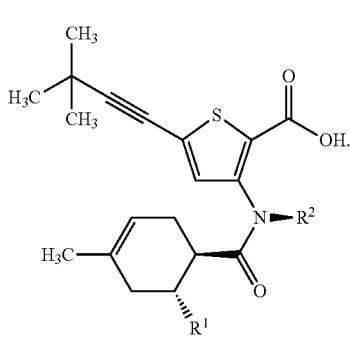

In one embodiment of the invention the compound of formula (I) is a compound of formula (Ir)-(Iy):

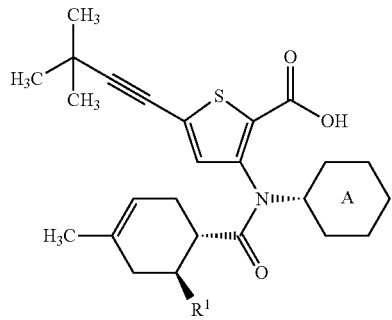
(Ir)

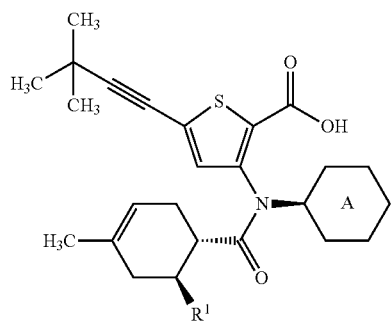
(Is)

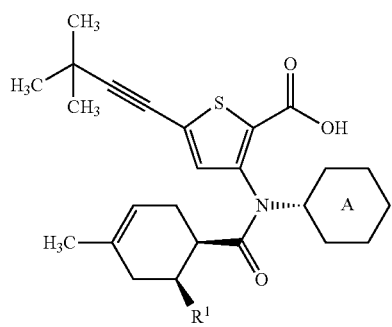
(It)

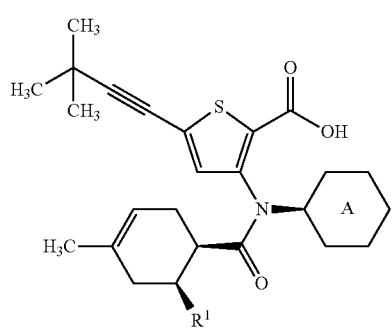
(Iu)

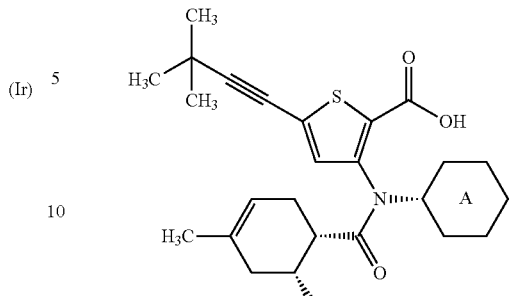
(Iv)

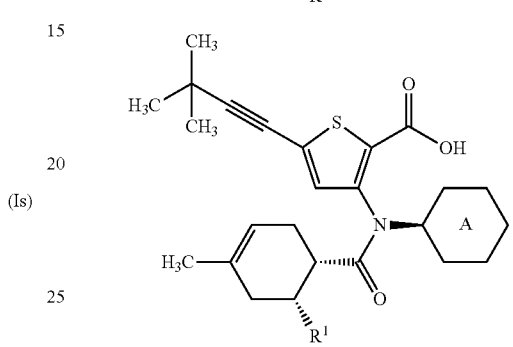
(Iw)

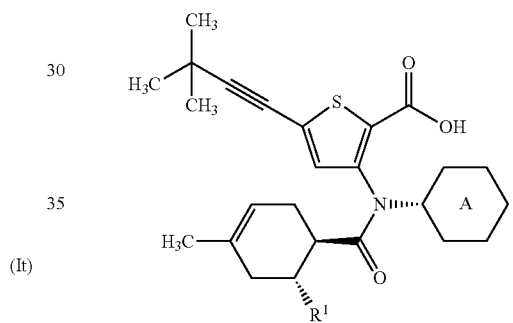
(Ix)

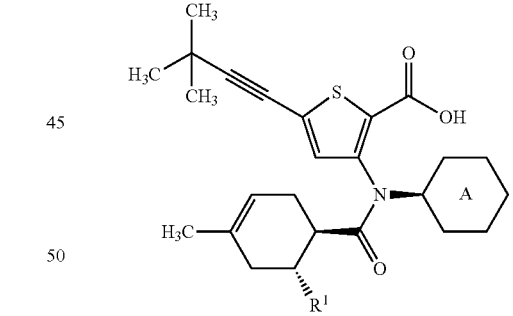
(Iy)

wherein the ring A is optionally substituted by one or more of: halogen, nitro, nitroso, SO3R12, PO3RcRd, CONR13R14, C1-6 alkyl, C2-6 alkenyl, C2-6 alkynyl, C6-12 aralkyl, C6-12 aryl, C1-6 alkyloxy, C2-6 alkenyloxy, C2-6 alkynyloxy, C6-12 aryloxy, C(O)C1-6 alkyl, C(O)C2-6 alkenyl, C(O) C2-6 alkynyl, C(O)C6-12 aryl, C(O)C6-12 aralkyl, C3-10 heterocycle, hydroxyl, NR13R14, C(O)OR12, cyano, azido, amidino or guanido; wherein R12, Rc, Rd, R13 and R14 are each independently chosen from H, C1-12 alkyl, C2-12 alkenyl, C2-12 alkynyl, C6-14 aryl, C3-12 heterocycle, C3-18 heteroaralkyl, C6-18 aralkyl; or Rc and Rd are taken together with the oxygens to form a 5 to 10 membered heterocycle; or $R^{13}$ and $R^{14}$ are taken together with the nitrogen to form a 3 to 10 membered heterocycle.

In one embodiment of the invention R¹ is H.

In one embodiment of the invention R¹ is methyl.

In one embodiment of the invention R² is (C1-C12)alkyl, (C2-C12)alkenyl, (C2-C12)alkynyl, wherein R² is optionally substituted by one or more of: halogen, nitro, nitroso, SO3R12, PO3RcRd, CONR13R14, C1-6 alkyl, C2-6 alkenyl, C2-6 alkynyl, C6-12 aralkyl, C6-12 aryl, C1-6 alkyloxy, C2-6 alkenyloxy, C2-6 alkynyloxy, C6-12 aryloxy, C(O)C1-6 alkyl, C(O)C2-6 alkenyl, C(O)C2-6 alkynyl, C(O)C6-12 aryl, C(O)C6-12 aralkyl, C3-10 heterocycle, hydroxyl, NR13R14, C(O)OR12, cyano, azido, amidino or guanido; wherein R12, Rc, Rd, R13 and R14 are each independently chosen from H, C1-12 alkyl, C2-12 alkenyl, C2-12 alkynyl, C6-14 aryl, C3-12 heterocycle, C3-18 heteroaralkyl, C6-18 aralkyl; or Rc and Rd are taken together with the oxygens to form a 5 to 10 membered heterocycle; or R¹³ and R¹⁴ are taken together with the nitrogen to form a 3 to 10 membered heterocycle.

In one embodiment of the invention R² is aryl or aralkyl, wherein R² is optionally substituted by one or more of: halogen, nitro, nitroso, SO3R12, PO3RcRd, CONR13R14, C1-6 alkyl, C2-6 alkenyl, C2-6 alkynyl, C6-12 aralkyl, C6-12 aryl, C1-6 alkyloxy, C2-6 alkenyloxy, C2-6 alkynyloxy, C6-12 aryloxy, C(O)C1-6 alkyl, C(O)C2-6 alkenyl, C(O)C2-6 alkynyl, C(O)C6-12 aryl, C(O)C6-12 aralkyl, C3-10 heterocycle, hydroxyl, NR13R14, C(O)OR12, cyano, azido, amidino or guanido; wherein R12, Rc, Rd, R13 and R14 are each independently chosen from H, C1-12 alkyl, C2-12 alkenyl, C2-12 alkynyl, C6-14 aryl, C3-12 heterocycle, C3-18 heteroaralkyl, C6-18 aralkyl; or Rc and Rd are taken together with the oxygens to form a 5 to 10 membered heterocycle; or R13 and R14 are taken together with the nitrogen to form a 3 to 10 membered heterocycle.

In one embodiment of the invention R² is heterocycle or heteroaralkyl, wherein R² is optionally substituted by one or more of: halogen, nitro, nitroso, SO3R12, PO3RcRd, CONR13R14, C1-6 alkyl, C2-6 alkenyl, C2-6 alkynyl, C6-12 aralkyl, C6-12 aryl, C1-6 alkyloxy, C2-6 alkenyloxy, C2-6 alkynyloxy, C6-12 aryloxy, C(O)C1-6 alkyl, C(O)C2-6 alkenyl, C(O)C2-6 alkynyl, C(O)C6-12 aryl, C(O)C6-12 aralkyl, C3-10 heterocycle, hydroxyl, NR13R14, C(O)OR12, cyano, azido, amidino or guanido; wherein R12, Rc, Rd, R13 and R14 are each independently chosen from H, C1-12 alkyl, C2-12 alkenyl, C2-12 alkynyl, C6-14 aryl, C3-12 heterocycle, C3-18 heteroaralkyl, C6-18 aralkyl; or Rc and Rd are taken together with the oxygens to form a 5 to 10 membered heterocycle; or R13 and R14 are taken together with the nitrogen to form a 3 to 10 membered heterocycle.

In one embodiment of the invention R² is selected from:

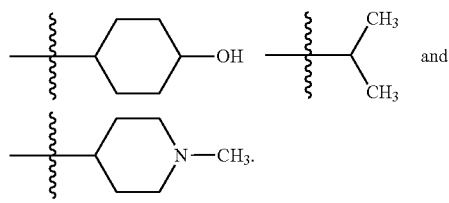

In one embodiment of the invention R² is:

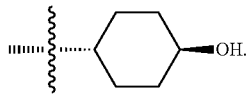

In one embodiment of the invention R² is isopropyl.

As will be appreciated by those skilled in the art, the compounds of the present invention may exist in solvated or hydrated form. The scope of the present invention includes such forms. Again, as will be appreciated by those skilled in the art, the compounds may be capable of esterification. The scope of the present invention includes esters and other physiologically functional derivatives. The scope of the present invention includes prodrug forms of the compound herein described.

"Ester" means any ester of a compound in which any of the —COOH functions of the molecule is replaced by a —C(O)OR function, or in which any of the —OH functions of the molecule are replaced with a —OC(O)R function, in which the R moiety of the ester is any carbon-containing group which forms a stable ester moiety, including but not limited to alkyl, alkenyl, alkynyl, cycloalkyl, cycloalkylalkyl, aryl, arylalkyl, heterocyclyl, heterocyclylalkyl and substituted derivatives thereof.

The term "prodrug" as used herein refers to any compound that when administered to a biological system generates the drug substance, i.e., active ingredient, as a result of spontaneous chemical reaction(s), enzyme catalyzed chemical reaction(s), photolysis, and/or metabolic chemical reaction(s). A prodrug is thus a covalently modified analog or latent form of a therapeutically active compound. Non-limiting examples of prodrugs include ester moieties, quaternary ammonium moieties, glycol moieties, and the like.

One skilled in the art will recognize that substituents and other moieties of the compounds of Formula I or II should be selected in order to provide a compound which is sufficiently stable to provide a pharmaceutically useful compound which can be formulated into an acceptably stable pharmaceutical composition. Compounds of Formula I or II which have such stability are contemplated as falling within the scope of the present invention.

A compound of Formula I and its pharmaceutically acceptable salts may exist as different polymorphs or pseudopolymorphs. As used herein, crystalline polymorphism means the ability of a crystalline compound to exist in different crystal structures. Polymorphism generally can occur as a response to changes in temperature, pressure, or both. Polymorphism can also result from variations in the crystallization process. Polymorphs can be distinguished by various physical characteristics known in the art such as x-ray diffraction patterns, solubility, and melting point. The crystalline polymorphism may result from differences in crystal packing (packing polymorphism) or differences in packing between different conformers of the same molecule (conformational polymorphism). As used herein, crystalline pseudopolymorphism means the ability of a hydrate or solvate of a compound to exist in different crystal structures. The pseudopolymorphs of the instant invention may exist due to differences in crystal packing (packing pseudopolymorphism) or due to differences in packing between different conformers of the same molecule (conformational pseudopolymorphism). The instant invention comprises all polymorphs and pseudopolymorphs of the compounds of Formula I and their pharmaceutically acceptable salts.

A compound of Formula I and its pharmaceutically acceptable salts may also exist as an amorphous solid. As used herein, an amorphous solid is a solid in which there is no long-range order of the positions of the atoms in the solid. This definition applies as well when the crystal size is two nanometers or less. Additives, including solvents, may be used to create the amorphous forms of the instant invention. The instant invention comprises all amorphous forms of the compounds of Formula I and their pharmaceutically acceptable salts.

Certain of the compounds described herein contain one or more chiral centers, or may otherwise be capable of existing as multiple stereoisomers. The scope of the present invention includes mixtures of stereoisomers as well as purified enantiomers or enantiomerically/diastereomerically enriched mixtures. Also included within the scope of the invention are the individual isomers of the compounds represented by the formulae of the present invention, as well as any wholly or partially equilibrated mixtures thereof. The present invention also includes the individual isomers of the compounds represented by the formulas above as mixtures with isomers thereof in which one or more chiral centers are inverted.

"Diastereomer" refers to a stereoisomer with two or more centers of chirality and whose molecules are not mirror images of one another. Diastereomers have different physical properties, e.g., melting points, boiling points, spectral properties, and reactivities. Mixtures of diastereomers may separate under high resolution analytical procedures such as electrophoresis and chromatography.

"Atropisomers" refer to stereoisomers of a compound resulting from hindered rotation about single bonds where the steric strain barrier to rotation is high enough to allow for the isolation of the individual conformer. Atropisomers display axial chirality.

Atropisomers may be equilibrated thermally and the interconversion barrier may be measured kinetically. Atropisomerism may occur apart from the presence of other forms of chiral isomerism. Thus, as illustrated, the depicted nitrogen atom is planar and compound of Formula I is capable of existing as atropisomers:

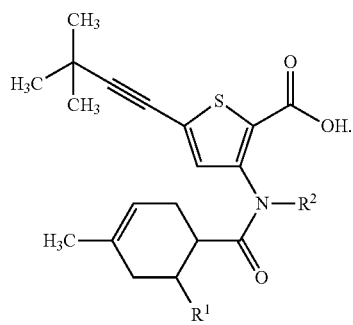

(I)

In one embodiment of the present invention, the compounds exist in a conformeric form of Formula Ig:

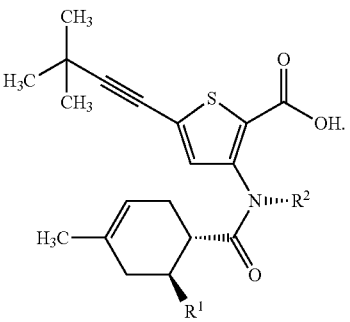

(Ig)

Stereochemical definitions and conventions used herein generally follow S. P. Parker, Ed., *McGraw-Hill Dictionary of Chemical Terms* (1984) McGraw-Hill Book Company, New York; and Eliel, E. and Wilen, S., *Stereochemistry of Organic Compounds* (1994) John Wiley & Sons, Inc., New York.

The present invention includes a salt or solvate of the compounds herein described, including combinations thereof such as a solvate of a salt. The compounds of the present invention may exist in solvated, for example hydrated, as well as unsolvated forms, and the present invention encompasses all such forms.

Typically, but not absolutely, the salts of the present invention are pharmaceutically acceptable salts. Salts encompassed within the term "pharmaceutically acceptable salts" refer to non-toxic salts of the compounds of this invention.

Examples of suitable pharmaceutically acceptable salts include inorganic acid addition salts such as chloride, bromide, sulfate, phosphate, and nitrate; organic acid addition salts such as acetate, galactarate, propionate, succinate, lactate, glycolate, malate, tartrate, citrate, maleate, fumarate, methanesulfonate, p-toluenesulfonate, and ascorbate; salts with acidic amino acid such as aspartate and glutamate; alkali metal salts such as sodium salt and potassium salt; alkaline earth metal salts such as magnesium salt and calcium salt; ammonium salt; organic basic salts such as trimethylamine salt, triethylamine salt, pyridine salt, picoline salt, dicyclohexylamine salt, and N,N'-dibenzylethylenediamine salt; and salts with basic amino acid such as lysine salt and arginine salt. The salts may be in some cases hydrates or ethanol solvates.

The compounds of the invention can also exist as tautomeric isomers in certain cases. Although only one delocalized resonance structure may be depicted, all such forms are contemplated within the scope of the invention. For example, ene-amine tautomers can exist for purine, pyrimidine, imidazole, guanidine, amidine, and tetrazole systems and all their possible tautomeric forms are within the scope of the invention.

Selected substituents comprising the compounds of Formula I may be present to a recursive degree. In this context, "recursive substituent" means that a substituent may recite another instance of itself. The multiple recitations may be direct or indirect through a sequence of other substituents. Because of the recursive nature of such substituents, theoretically, a large number of compounds may be present in any given embodiment. One of ordinary skill in the art of medicinal chemistry understands that the total number of such substituents is reasonably limited by the desired properties of the compound intended. Such properties include, by way of example and not limitation, physical properties such as molecular weight, solubility or log P, application properties such as activity against the intended target, and practical properties such as ease of synthesis. Recursive substituents may be an intended aspect of the invention. One of ordinary skill in the art of medicinal chemistry understands the versatility of such substituents. To the degree that recursive substituents are present in an embodiment of the invention, they may recite another instance of themselves, 0, 1, 2, 3, or 4 times.

The compounds of Formula I also include molecules that incorporate isotopes of the atoms specified in the particular molecules. Non-limiting examples of these isotopes include D, T, $^{14}C$, $^{13}C$ and $^{15}N$.

Protecting Groups

In the context of the present invention, protecting groups include prodrug moieties and chemical protecting groups.

Protecting groups are available, commonly known and used, and are optionally used to prevent side reactions with the protected group during synthetic procedures, i.e. routes or methods to prepare the compounds of the invention. For the most part the decision as to which groups to protect, when to do so, and the nature of the chemical protecting group "PG" will be dependent upon the chemistry of the reaction to be protected against (e.g., acidic, basic, oxidative, reductive or other conditions) and the intended direction of the synthesis. The PG groups do not need to be, and generally are not, the same if the compound is substituted with multiple PG. In general, PG will be used to protect functional groups such as carboxyl, hydroxyl, thio, or amino groups and to thus prevent side reactions or to otherwise facilitate the synthetic efficiency. The order of deprotection to yield free, deprotected groups is dependent upon the intended direction of the synthesis and the reaction conditions to be encountered, and may occur in any order as determined by the artisan.

Various functional groups of the compounds of the invention may be protected. For example, protecting groups for —OH groups (whether hydroxyl, carboxylic acid, phosphonic acid, or other functions) include "ether- or ester-forming groups". Ether- or ester-forming groups are capable of functioning as chemical protecting groups in the synthetic schemes set forth herein. However, some hydroxyl and thio protecting groups are neither ether- nor ester-forming groups, as will be understood by those skilled in the art, and are included with amides, discussed below.

A very large number of hydroxyl protecting groups and amide-forming groups and corresponding chemical cleavage reactions are described in *Protective Groups in Organic Synthesis*, Theodora W. Greene and Peter G. M. Wuts (John Wiley & Sons, Inc., New York, 1999, ISBN 0-471-16019-9) ("Greene"). See also Kocienski, Philip J.; *Protecting Groups* (Georg Thieme Verlag Stuttgart, New York, 1994), which is incorporated by reference in its entirety herein. In particular Chapter 1, Protecting Groups: An Overview, pages 1-20, Chapter 2, Hydroxyl Protecting Groups, pages 21-94, Chapter 3, Diol Protecting Groups, pages 95-117, Chapter 4, Carboxyl Protecting Groups, pages 118-154, Chapter 5, Carbonyl Protecting Groups, pages 155-184. For protecting groups for carboxylic acid, phosphonic acid, phosphonate, sulfonic acid and other protecting groups for acids see Greene as set forth below. Such groups include by way of example and not limitation, esters, amides, hydrazides, and the like.

Ether- and Ester-Forming Protecting Groups

Ester-forming groups include: (1) phosphonate ester-forming groups, such as phosphonamidate esters, phosphorothioate esters, phosphonate esters, and phosphon-bis-amidates; (2) carboxyl ester-forming groups, and (3) sulphur ester-forming groups, such as sulphonate, sulfate, and sulfinate.

Metabolites of the Compounds of the Invention

Also falling within the scope of this invention are the in vivo metabolic products of the compounds described herein. Such products may result for example from the oxidation, reduction, hydrolysis, amidation, esterification and the like of the administered compound, primarily due to enzymatic processes. Accordingly, the invention includes compounds produced by a process comprising contacting a compound of this invention with a mammal for a period of time sufficient to yield a metabolic product thereof. Such products typically are identified by preparing a radiolabelled (e.g., C14 or H3) compound of the invention, administering it parenterally in a detectable dose (e.g., greater than about 0.5 mg/kg) to an animal such as rat, mouse, guinea pig, monkey, or to man, allowing sufficient time for metabolism to occur (typically about 30 seconds to 30 hours) and isolating its conversion products from the urine, blood or other biological samples. These products are easily isolated since they are labeled (others are isolated by the use of antibodies capable of binding epitopes surviving in the metabolite). The metabolite structures are determined in conventional fashion, e.g., by MS or NMR analysis. In general, analysis of metabolites is done in the same way as conventional drug metabolism studies well-known to those skilled in the art. The conversion products, so long as they are not otherwise found in vivo, are useful in diagnostic assays for therapeutic dosing of the compounds of the invention even if they possess no anti-infective activity of their own.

The definitions and substituents for various genus and sub-genus of the present compounds are described and illustrated herein. It should be understood by one skilled in the art that any combination of the definitions and substituents described above should not result in an inoperable species or compound. "Inoperable species or compounds" means compound structures that violates relevant scientific principles (such as, for example, a carbon atom connecting to more than four covalent bonds) or compounds too unstable to permit isolation and formulation into pharmaceutically acceptable dosage forms.

Pharmaceutical Formulations

The compounds of this invention are formulated with conventional carriers and excipients, which will be selected in accord with ordinary practice. Tablets will contain excipients, glidants, fillers, binders and the like. Aqueous formulations are prepared in sterile form, and when intended for delivery by other than oral administration generally will be isotonic. All formulations will optionally contain excipients such as those set forth in the Handbook of Pharmaceutical Excipients (1986), herein incorporated by reference in its entirety. Excipients include ascorbic acid and other antioxidants, chelating agents such as EDTA, carbohydrates such as dextrin, hydroxyalkylcellulose, hydroxyalkylmethylcellulose, stearic acid and the like. The pH of the formulations ranges from about 3 to about 11, but is ordinarily about 7 to 10.

While it is possible for the active ingredients to be administered alone it may be preferable to present them as pharmaceutical formulations. The formulations of the invention, both for veterinary and for human use, comprise at least one active ingredient, together with one or more acceptable carriers and optionally other therapeutic ingredients. The carrier(s) must be "acceptable" in the sense of being compatible with the other ingredients of the formulation and physiologically innocuous to the recipient thereof.

The formulations include those suitable for the foregoing administration routes. The formulations may conveniently be presented in unit dosage form and may be prepared by any of the methods well known in the art of pharmacy. Techniques and formulations generally are found in Remington's Pharmaceutical Sciences (Mack Publishing Co., Easton, Pa.), herein incorporated by reference in its entirety. Such methods include the step of bringing into association the active ingredient with the carrier which constitutes one or more accessory ingredients. In general the formulations are prepared by uniformly and intimately bringing into association the active ingredient with liquid carriers or finely divided solid carriers or both, and then, if necessary, shaping the product.

Formulations of the present invention suitable for oral administration may be presented as discrete units such as capsules, cachets or tablets each containing a predetermined amount of the active ingredient; as a powder or granules; as a solution or a suspension in an aqueous or non-aqueous liquid; or as an oil-in-water liquid emulsion or a water-in-oil liquid emulsion. The active ingredient may also be administered as a bolus, electuary or paste.

A tablet is made by compression or molding, optionally with one or more accessory ingredients. Compressed tablets may be prepared by compressing in a suitable machine the active ingredient in a free-flowing form such as a powder or granules, optionally mixed with a binder, lubricant, inert diluent, preservative, surface active or dispersing agent. Molded tablets may be made by molding in a suitable machine a mixture of the powdered active ingredient moistened with an inert liquid diluent. The tablets may optionally be coated or scored and optionally are formulated so as to provide slow or controlled release of the active ingredient.

For administration to the eye or other external tissues e.g., mouth and skin, the formulations are preferably applied as a topical ointment or cream containing the active ingredient(s) in an amount of, for example, 0.075 to 20% w/w (including active ingredient(s) in a range between 0.1% and 20% in increments of 0.1% w/w such as 0.6% w/w, 0.7% w/w, etc.), preferably 0.2 to 15% w/w and most preferably 0.5 to 10% w/w. When formulated in an ointment, the active ingredients may be employed with either a paraffinic or a water-miscible ointment base. Alternatively, the active ingredients may be formulated in a cream with an oil-in-water cream base.

If desired, the aqueous phase of the cream base may include, for example, at least 30% w/w of a polyhydric alcohol, i.e. an alcohol having two or more hydroxyl groups such as propylene glycol, butane 1,3-diol, mannitol, sorbitol, glycerol and polyethylene glycol (including PEG 400) and mixtures thereof. The topical formulations may desirably include a compound which enhances absorption or penetration of the active ingredient through the skin or other affected areas. Examples of such dermal penetration enhancers include dimethyl sulphoxide and related analogs.

The oily phase of the emulsions of this invention may be constituted from known ingredients in a known manner. While the phase may comprise merely an emulsifier (otherwise known as an emulgent), it desirably comprises a mixture of at least one emulsifier with a fat or an oil or with both a fat and an oil. Preferably, a hydrophilic emulsifier is included together with a lipophilic emulsifier which acts as a stabilizer. It is also preferred to include both an oil and a fat. Together, the emulsifier(s) with or without stabilizer(s) make up the so-called emulsifying wax, and the wax together with the oil and fat make up the so-called emulsifying ointment base which forms the oily dispersed phase of the cream formulations.

Emulgents and emulsion stabilizers suitable for use in the formulation of the invention include Tween® 60, Span® 80, cetostearyl alcohol, benzyl alcohol, myristyl alcohol, glyceryl mono-stearate and sodium lauryl sulfate.

The choice of suitable oils or fats for the formulation is based on achieving the desired cosmetic properties. The cream should preferably be a non-greasy, non-staining and washable product with suitable consistency to avoid leakage from tubes or other containers. Straight or branched chain, mono- or dibasic alkyl esters such as di-isoadipate, isocetyl stearate, propylene glycol diester of coconut fatty acids, isopropyl myristate, decyl oleate, isopropyl palmitate, butyl stearate, 2-ethylhexyl palmitate or a blend of branched chain esters known as Crodamol CAP may be used, the last three being preferred esters. These may be used alone or in combination depending on the properties required. Alternatively, high melting point lipids such as white soft paraffin and/or liquid paraffin or other mineral oils are used.

Pharmaceutical formulations according to the present invention comprise one or more compounds of the invention together with one or more pharmaceutically acceptable carriers or excipients and optionally other therapeutic agents. Pharmaceutical formulations containing the active ingredient may be in any form suitable for the intended method of administration. When used for oral use for example, tablets, troches, lozenges, aqueous or oil suspensions, dispersible powders or granules, emulsions, hard or soft capsules, syrups or elixirs may be prepared. Compositions intended for oral use may be prepared according to any method known to the art for the manufacture of pharmaceutical compositions and such compositions may contain one or more agents including sweetening agents, flavoring agents, coloring agents and preserving agents, in order to provide a palatable preparation. Tablets containing the active ingredient in admixture with non-toxic pharmaceutically acceptable excipient which are suitable for manufacture of tablets are acceptable. These excipients may be, for example, inert diluents, such as calcium or sodium carbonate, lactose, lactose monohydrate, croscarmellose sodium, povidone, calcium or sodium phosphate; granulating and disintegrating agents, such as maize starch, or alginic acid; binding agents, such as cellulose, microcrystalline cellulose, starch, gelatin or acacia; and lubricating agents, such as magnesium stearate, stearic acid or talc. Tablets may be uncoated or may be coated by known techniques including microencapsulation to delay disintegration and adsorption in the gastrointestinal tract and thereby provide a sustained action over a longer period. For example, a time delay material such as glyceryl monostearate or glyceryl distearate alone or with a wax may be employed.

Formulations for oral use may be also presented as hard gelatin capsules where the active ingredient is mixed with an inert solid diluent, for example calcium phosphate or kaolin, or as soft gelatin capsules wherein the active ingredient is mixed with water or an oil medium, such as peanut oil, liquid paraffin or olive oil.

Aqueous suspensions of the invention contain the active materials in admixture with excipients suitable for the manufacture of aqueous suspensions. Such excipients include a suspending agent, such as sodium carboxymethylcellulose, methylcellulose, hydroxypropyl methylcelluose, sodium alginate, polyvinylpyrrolidone, gum tragacanth and gum acacia, and dispersing or wetting agents such as a naturally occurring phosphatide (e.g., lecithin), a condensation product of an alkylene oxide with a fatty acid (e.g., polyoxyethylene stearate), a condensation product of ethylene oxide with a long chain aliphatic alcohol (e.g., heptadecaethyleneoxycetanol), a condensation product of ethylene oxide with a partial ester derived from a fatty acid and a hexitol anhydride (e.g., polyoxyethylene sorbitan monooleate). The aqueous suspension may also contain one or more preservatives such as ethyl or n-propyl p-hydroxy-benzoate, one or more coloring agents, one or more flavoring agents and one or more sweetening agents, such as sucrose or saccharin.

Oil suspensions may be formulated by suspending the active ingredient in a vegetable oil, such as arachis oil, olive oil, sesame oil or coconut oil, or in a mineral oil such as liquid paraffin. The oral suspensions may contain a thickening agent, such as beeswax, hard paraffin or cetyl alcohol. Sweetening agents, such as those set forth herein, and flavoring agents may be added to provide a palatable oral preparation. These compositions may be preserved by the addition of an antioxidant such as ascorbic acid.

Dispersible powders and granules of the invention suitable for preparation of an aqueous suspension by the addition of water provide the active ingredient in admixture with a dispersing or wetting agent, a suspending agent, and one or more preservatives. Suitable dispersing or wetting agents and suspending agents are exemplified by those disclosed above. Additional excipients, for example sweetening, flavoring and coloring agents, may also be present.

The pharmaceutical compositions of the invention may also be in the form of oil-in-water emulsions. The oily phase may be a vegetable oil, such as olive oil or arachis oil, a mineral oil, such as liquid paraffin, or a mixture of these. Suitable emulsifying agents include naturally-occurring gums, such as gum acacia and gum tragacanth, naturally occurring phosphatides, such as soybean lecithin, esters or partial esters derived from fatty acids and hexitol anhydrides, such as sorbitan monooleate, and condensation products of these partial esters with ethylene oxide, such as polyoxyethylene sorbitan monooleate. The emulsion may also contain sweetening and flavoring agents. Syrups and elixirs may be formulated with sweetening agents, such as glycerol, sorbitol or sucrose. Such formulations may also contain a demulcent, a preservative, a flavoring or a coloring agent.

The pharmaceutical compositions of the invention may be in the form of a sterile injectable preparation, such as a sterile injectable aqueous or oleaginous suspension. This suspension may be formulated according to the known art using those suitable dispersing or wetting agents and suspending agents which have been mentioned herein. The sterile injectable preparation may also be a sterile injectable solution or suspension in a non-toxic parenterally acceptable diluent or solvent, such as a solution in 1,3-butane-diol or prepared as a lyophilized powder. Among the acceptable vehicles and solvents that may be employed are water, Ringer's solution and isotonic sodium chloride solution. In addition, sterile fixed oils may conventionally be employed as a solvent or suspending medium. For this purpose any bland fixed oil may be employed including synthetic mono- or diglycerides. In addition, fatty acids such as oleic acid may likewise be used in the preparation of injectables.

The amount of active ingredient that may be combined with the carrier material to produce a single dosage form will vary depending upon the host treated and the particular mode of administration. For example, a time-release formulation intended for oral administration to humans may contain approximately 1 to 1000 mg of active material compounded with an appropriate and convenient amount of carrier material which may vary from about 5 to about 95% of the total compositions (weight:weight). The pharmaceutical composition can be prepared to provide easily measurable amounts for administration. For example, an aqueous solution intended for intravenous infusion may contain from about 3 to 500 μg of the active ingredient per milliliter of solution in order that infusion of a suitable volume at a rate of about 30 mL/hr can occur.

Formulations suitable for administration to the eye include eye drops wherein the active ingredient is dissolved or suspended in a suitable carrier, especially an aqueous solvent for the active ingredient. The active ingredient is preferably present in such formulations in a concentration of 0.5 to 20%, advantageously 0.5 to 10% particularly about 1.5% w/w.

Formulations suitable for topical administration in the mouth include lozenges comprising the active ingredient in a flavored basis, usually sucrose and acacia or tragacanth; pastilles comprising the active ingredient in an inert basis such as gelatin and glycerin, or sucrose and acacia; and mouthwashes comprising the active ingredient in a suitable liquid carrier.

Formulations for rectal administration may be presented as a suppository with a suitable base comprising for example cocoa butter or a salicylate.

Formulations suitable for intrapulmonary or nasal administration have a particle size for example in the range of 0.1 to 500 μm (including particle sizes in a range between 0.1 and 500 μm in increments such as 0.5 μm, 1 μm, 30 μm, 35 μm, etc.), which is administered by rapid inhalation through the nasal passage or by inhalation through the mouth so as to reach the alveolar sacs. Suitable formulations include aqueous or oily solutions of the active ingredient. Formulations suitable for aerosol or dry powder administration may be prepared according to conventional methods and may be delivered with other therapeutic agents such as compounds heretofore used in the treatment or prophylaxis of infections as described herein.

Formulations suitable for vaginal administration may be presented as pessaries, tampons, creams, gels, pastes, foams or spray formulations containing in addition to the active ingredient such carriers as are known in the art to be appropriate.

Formulations suitable for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents.

The formulations are presented in unit-dose or multi-dose containers, for example sealed ampoules and vials, and may be stored in a freeze-dried (lyophilized) condition requiring only the addition of the sterile liquid carrier, for example water for injection, immediately prior to use. Extemporaneous injection solutions and suspensions are prepared from sterile powders, granules and tablets of the kind previously described. Preferred unit dosage formulations are those containing a daily dose or unit daily sub-dose, as herein above recited, or an appropriate fraction thereof, of the active ingredient.

It should be understood that in addition to the ingredients particularly mentioned above the formulations of this invention may include other agents conventional in the art having regard to the type of formulation in question, for example those suitable for oral administration may include flavoring agents.

Compounds of the invention can also be formulated to provide controlled release of the active ingredient to allow less frequent dosing or to improve the pharmacokinetic or toxicity profile of the active ingredient. Accordingly, the invention also provided compositions comprising one or more compounds of the invention formulated for sustained or controlled release.

The effective dose of an active ingredient depends at least on the nature of the condition being treated, toxicity, whether the compound is being used prophylactically (lower doses) or against an active viral infection, the method of delivery, and the pharmaceutical formulation, and will be determined by the clinician using conventional dose escalation studies. The effective dose can be expected to be from about 0.0001 to about 100 mg/kg body weight per day; typically, from about 0.01 to about 10 mg/kg body weight per day; more typically, from about 0.01 to about 5 mg/kg body weight per day; most typically, from about 0.05 to about 0.5 mg/kg body weight per day. For example, the daily candidate dose for an adult human of approximately 70 kg body weight will range from 1 mg to 1000 mg, preferably between 5 mg and 500 mg, and may take the form of single or multiple doses.

Routes of Administration

One or more compounds of the invention (herein referred to as the active ingredients) are administered by any route appropriate to the condition to be treated. Suitable routes include oral, rectal, nasal, topical (including buccal and sublingual), vaginal and parenteral (including subcutaneous, intramuscular, intravenous, intradermal, intrathecal and epidural), and the like. It will be appreciated that the preferred route may vary with for example the condition of the recipient. An advantage of the compounds of this invention is that they are orally bioavailable and can be dosed orally.

Combination Therapy, Including HCV Combination Therapy

In another embodiment, the compounds of the present invention may be combined with one or more active agent. Non-limiting examples of suitable combinations include combinations of one or more compounds of the present invention with one or more interferons, ribavirin or its analogs, HCV NS3 protease inhibitors, NS5A inhibitors, alpha-glucosidase 1 inhibitors, hepatoprotectants, mevalonate decarboxylase antagonists, antagonists of the renin-angiotensin system, other anti-fibrotic agents, endothelin antagonists, nucleoside or nucleotide inhibitors of HCV NS5B polymerase, non-nucleoside inhibitors of HCV NS5B polymerase, HCV NS4B inhibitors, inhibitors of viral entry and/or assembly, TLR-7 agonists, cyclophilin inhibitors, HCV IRES inhibitors, pharmacokinetic enhancers and other drugs for treating HCV; or mixtures thereof.

More specifically, one or more compounds of the present invention may be combined with one or more compounds selected from the group consisting of 1) interferons, e.g., pegylated rIFN-alpha 2b (PEG-Intron), pegylated rIFN-alpha 2a (Pegasys), rIFN-alpha 2b (Intron A), rIFN-alpha 2a (Roferon-A), interferon alpha (MOR-22, OPC-18, Alfaferone, Alfanative, Multiferon, subalin), interferon alfacon-1 (Infergen), interferon alpha-n1 (Wellferon), interferon alpha-n3 (Alferon), interferon-beta (Avonex, DL-8234), interferon-omega (omega DUROS, Biomed 510), albinterferon alpha-2b (Albuferon), IFN alpha XL, BLX-883 (Locteron), DA-3021, glycosylated interferon alpha-2b (AVI-005), PEG-Infergen, PEGylated interferon lambda (PEGylated IL-29), and belerofon, 2) ribavirin and its analogs, e.g., ribavirin (Rebetol, Copegus), and taribavirin (Viramidine), 3) HCV NS3 protease inhibitors, e.g., boceprevir (SCH-503034, SCH-7), telaprevir (VX-950), VX-813, TMC-435 (TMC435350), ABT-450, BI-201335, BI-1230, MK-5172, MK-7009 (vaniprevir), SCH-900518, VBY-376, VX-500, GS-9256, GS-9451, BMS-790052, BMS-605339, PHX-1766, AS-101, YH-5258, YH5530, YH5531, and ITMN-191 (R-7227), 4) alpha-glucosidase 1 inhibitors, e.g., celgosivir (MX-3253), Miglitol, and UT-231B, 5) hepatoprotectants, e.g., emericasan (IDN-6556), ME-3738, GS-9450 (LB-84451), silibilin, and MitoQ, 6) nucleoside or nucleotide inhibitors of HCV NS5B polymerase and prodrugs thereof, e.g., GS-6620, R1626, R7128 (R4048), IDX184, IDX-102, PSI-7851, PSI-938, PSI-7977, BCX-4678, valopicitabine (NM-283), and MK-0608, 7) non-nucleoside inhibitors of HCV NS5B polymerase, e.g., filibuvir (PF-868554), ABT-333, ABT-072, BI-207127, VCH-759, VCH-916, JTK-652, MK-3281, VBY-708, VX-222, A848837, ANA-598, GL60667, GL59728, A-63890, A-48773, A-48547, BC-2329, VCH-796 (nesbuvir), GSK625433, BILN-1941, XTL-2125, and GS-9190 (tegobuvir), 8) HCV NS5A inhibitors, e.g., GS-5885, AZD-2836 (A-831), AZD-7295 (A-689), and BMS-790052, 9) TLR-7 agonists, e.g., imiquimod, 852A, GS-9524, GS-9620, ANA-773, ANA-975, AZD-8848 (DSP-3025), PF-04878691, and SM-360320, 10) cyclophilin inhibitors, e.g., DEBIO-025, SCY-635, and NIM811, 11) HCV IRES inhibitors, e.g., MCI-067, 12) pharmacokinetic enhancers, e.g., BAS-100, SPI-452, PF-4194477, TMC-41629, GS-9350 (cobicistat), GS-9585, and roxythromycin, 13) other drugs for treating HCV, e.g., thymosin alpha 1 (Zadaxin), nitazoxanide (Alinea, NTZ), BIVN-401 (virostat), PYN-17 (altirex), KPE02003002, actilon (CPG-10101), GS-9525, KRN-7000, civacir, GI-5005, XTL-6865, BIT225, PTX-111, ITX2865, TT-033i, ANA 971, NOV-205, tarvacin, EHC-18, VGX-410C, EMZ-702, AVI 4065, BMS-650032, BMS-791325, Bavituximab, MDX-1106 (ONO-4538), Oglufanide, FK-788, and VX-497 (merimepodib)

14) mevalonate decarboxylase antagonists, e.g., statins, HMGCoA synthase inhibitors (e.g., hymeglusin), squalene synthesis inhibitors (e.g., zaragozic acid);

15) angiotensin II receptor antagonists, e.g., losartan, irbesartan, olmesartan, candesartan, valsartan, telmisartan, eprosartan;

16) angiotensin-converting enzyme inhibitors, e.g., captopril, zofenopril, enalapril, ramipril, quinapril, perindopril, lisinopril, benazepril, fosinopril;

17) other anti-fibrotic agents, e.g., amiloride and 18) endothelin antagonists, e.g. bosentan and ambrisentan.

In yet another embodiment, the present application discloses pharmaceutical compositions comprising a compound of the present invention, or a pharmaceutically acceptable salt thereof, in combination with at least one additional active agent, and a pharmaceutically acceptable carrier or excipient. In yet another embodiment, the present application provides a combination pharmaceutical agent with two or more therapeutic agents in a unitary dosage form. Thus, it is also possible to combine any compound of the invention with one or more other active agents in a unitary dosage form.

The combination therapy may be administered as a simultaneous or sequential regimen. When administered sequentially, the combination may be administered in two or more administrations.

Co-administration of a compound of the invention with one or more other active agents generally refers to simultaneous or sequential administration of a compound of the invention and one or more other active agents, such that therapeutically effective amounts of the compound of the invention and one or more other active agents are both present in the body of the patient.

Co-administration includes administration of unit dosages of the compounds of the invention before or after administration of unit dosages of one or more other active agents, for example, administration of the compounds of the invention within seconds, minutes, or hours of the administration of one or more other active agents. For example, a unit dose of a compound of the invention can be administered first, followed within seconds or minutes by administration of a unit dose of one or more other active agents. Alternatively, a unit dose of one or more other active agents can be administered first, followed by administration of a unit dose of a compound of the invention within seconds or minutes. In some cases, it may be desirable to administer a unit dose of a compound of the invention first, followed, after a period of hours (e.g., 1-12 hours), by administration of a unit dose of one or more other active agents. In other cases, it may be desirable to administer a unit dose of one or more other active agents first, followed, after a period of hours (e.g., 1-12 hours), by administration of a unit dose of a compound of the invention.

The combination therapy may provide "synergy" and "synergistic effect", i.e. the effect achieved when the active ingredients used together is greater than the sum of the effects that results from using the compounds separately. A synergistic effect may be attained when the active ingredients are: (1) co-formulated and administered or delivered simultaneously in a combined formulation; (2) delivered by alternation or in parallel as separate formulations; or (3) by some other regimen. When delivered in alternation therapy, a synergistic effect may be attained when the compounds are administered or delivered sequentially, e.g., in separate tablets, pills or capsules, or by different injections in separate syringes. In general, during alternation therapy, an effective dosage of each active ingredient is administered sequentially, i.e. serially, whereas in combination therapy, effective dosages of two or more active ingredients are administered together.

As will be appreciated by those skilled in the art, when treating a viral infection such as HCV, such treatment may be characterized in a variety of ways and measured by a variety of endpoints. The scope of the present invention is intended to encompass all such characterizations.

SYNTHETIC EXAMPLES

Certain abbreviations and acronyms are used in describing the experimental details. Although most of these would be understood by one skilled in the art, Table 1 contains a list of many of these abbreviations and acronyms.

TABLE 1

List of abbreviations and acronyms.

| Abbreviation | Meaning |
|---|---|
| DCM | dichloromethane |
| deg | Degrees Celsius |
| DMSO | dimethylsulfoxide |
| DMF | dimethylformamide |
| EtOAc | ethyl acetate |
| h or hr | hours |
| HPLC | High pressure liquid chromatography |
| LDA | lithium diisopropylamide |
| MeOH | methanol |
| Min | minutes |
| m/z | mass to charge ratio |
| MH+ | mass plus 1 |
| MH− | mass minus 1 |
| MS or ms | mass spectrum |
| Ph | phenyl |
| rt or r.t. | room temperature |
| TFA | trifluoroacetic acid |
| TLC or tlc | thin layer chromatography |
| δ | parts per million down field from tetramethylsilane |

The compounds of this invention may be synthesized by methods similar to those described in WO2011031669 and US20110020278.

Names of compounds and stereochemical assignments herein were generated using ChemBioDraw Ultra™ version 11.0.

Unless specified otherwise, retention times refer to an analytical HPLC method using a gradient of 2-98% acetonitrile (containing 0.05% trifluoroacetic acid) in water (containing 0.05% trifluoroacetic acid) over 5 minutes at a flow rate of 2 mL/min on a Phenomenex Gemini column (5μ, 80A, 50×4.6 mm).

SPECIFIC EXAMPLES

Examples 1 and 2

5-(3,3-Dimethylbut-1-ynyl)-3-((1S,6R)—N-isopropyl-4,6-dimethylcyclohex-3-enecarboxamido)thiophene-2-carboxylic acid and 5-(3,3-dimethylbut-1-ynyl)-3-((1R,6R)—N-isopropyl-4,6-dimethylcyclohex-3-enecarboxamido)thiophene-2-carboxylic acid Example 1

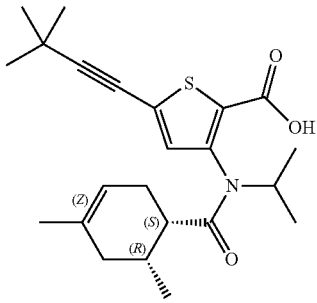

Example 2

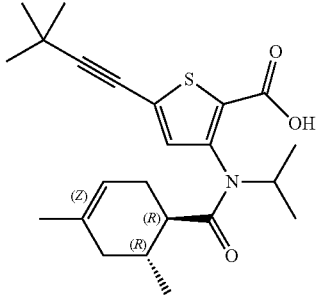

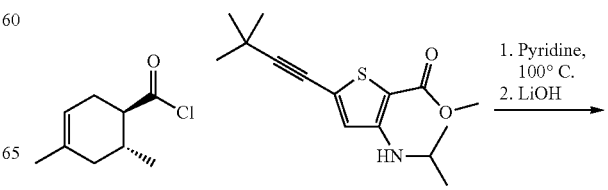

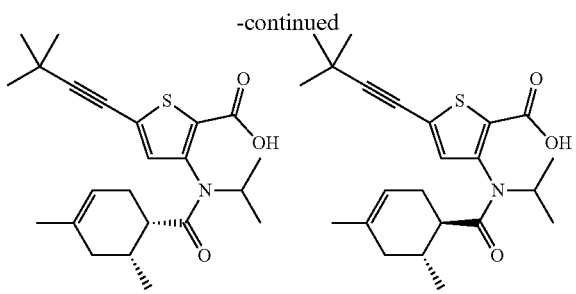

A solution of methyl 5-(3,3-dimethylbut-1-ynyl)-3-(isopropylamino)thiophene-2-carboxylate (140 mg, 0.5 mmol) in 1 mL of pyridine was treated with (1R,6R)-4,6-dimethylcyclohex-3-enecarbonyl chloride (172 mg, 1 mmol) and heated for 16 h at 100° C. in a sealed tube. The reaction mixture was cooled to room temperature, concentrated and purified by silica gel column chromatography (4 g pre-packed column, eluting with 0-20% hexane:ethylacetate) to separate the resulting mixture of diastereomers. The first peak to elute, methyl 5-(3,3-dimethylbut-1-ynyl)-3-((1S,6R)—N-isopropyl-4,6-dimethylcyclohex-3-enecarboxamido)thiophene-2-carboxylate, was treated with LiOH (5 equiv, THF/water 1:1) and purified by HPLC to give Example 1,5-(3,3-dimethylbut-1-ynyl)-3-((1S,6R)—N-isopropyl-4,6-dimethylcyclohex-3-enecarboxamido)thiophene-2-carboxylic acid: MS (m/z): 403.0 [M+H]$^+$; HPLC retention time 8.72 min (2-98% acetonitrile: water with 0.05% trifluoroacetic acid). The second peak to elute, methyl 5-(3,3-dimethylbut-1-ynyl)-3-((1R,6R)—N-isopropyl-4,6-dimethylcyclohex-3-enecarboxamido) thiophene-2-carboxylate, was treated with LiOH (5 equiv, THF/water 1:1) and purified by HPLC to give Example 2,5-(3,3-dimethylbut-1-ynyl)-3-((1R,6R)—N-isopropyl-4,6-dimethylcyclohex-3-enecarboxamido)thiophene-2-carboxylic acid: MS (m/z): 403.0 [M+H]$^+$; HPLC retention time 8.62 min (2-98% acetonitrile: water with 0.05% trifluoroacetic acid).

Synthesis of (1R,6R)-4,6-dimethyl-cyclohex-3-enecarboxylic acid chloride

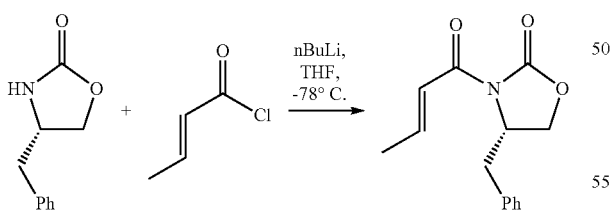

(S)-4-benzyloxazolidin-2-one (35 g, 0.2 mol) was dissolved in THF (500 mL) and cooled to −78° C. To this solution was added a solution of nBuLi in hexanes (80 mL, 0.2 mol) dropwise. The solution was stirred at this temperature for 30 min and then (E)-but-2-enoyl chloride (19 mL, 0.2 mol) was added slowly. The cold bath was removed and the reaction was allowed to stir at room temperature for 1 h. Upon completion of the reaction, saturated NH$_4$Cl solution was added to quench the reaction. Most THF was removed under vacuum distillation and the mixture was partitioned between ether and brine. After drying over Na$_2$SO$_4$, the organic layer was concentrated to give crude product which was purified by silica gel chromatography (20% EtOAc in hexanes) to give product (39 g, 79% yield) as a white solid.

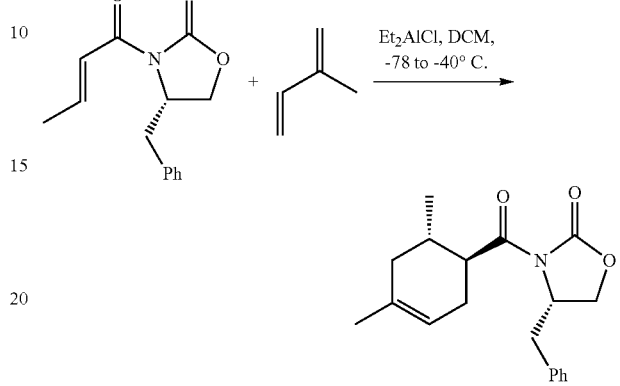

A solution of (S,E)-4-benzyl-3-but-2-enoyloxazolidin-2-one (34.5 g, 0.14 mol) and isoprene (250 mL) in DCM was cooled to −78° C. To this solution was added a solution of Et$_2$AlCl in toluene (100 mL, 0.18 mol) dropwise. The solution was warmed to −40° C. and stirred at this temperature overnight. Upon completion of the reaction, 2 N HCl solution (150 mL) was added to quench the reaction. Most DCM was removed under vacuum distillation and the mixture was extracted with ether. After drying over Na$_2$SO$_4$, the combined organic layer was concentrated to give crude product which was purified by silica gel chromatography (0-30% EtOAc in hexanes) to give product (39 g, 88% yield) as a crystalline white solid. Subsequent steps to generate the desired acid chloride were performed in a manner similar to those described for the synthesis of (1S,6S)-4,6-dimethyl-cyclohex-3-enecarboxylic acid chloride (see below).

Examples 3 and 4

5-(3,3-Dimethylbut-1-ynyl)-3-((1S,6S)—N-isopropyl-4,6-dimethylcyclohex-3-enecarboxamido) thiophene-2-carboxylic acid and 5-(3,3-dimethylbut-1-ynyl)-3-((1R,6S)—N-isopropyl-4,6-dimethylcyclohex-3-enecarboxamido)thiophene-2-carboxylic acid Example 3

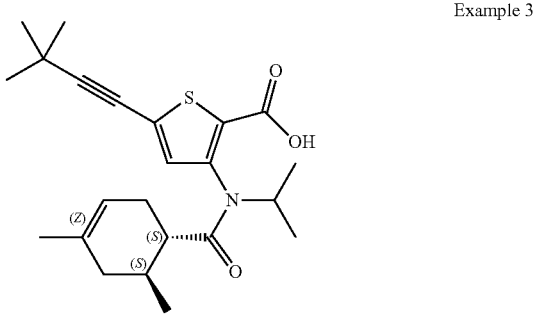

Example 4

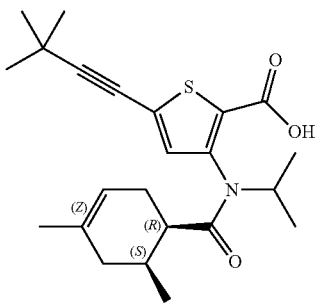

These compounds were synthesized in a manner similar to Examples 1 and 2, starting with (1S,6S)-4,6-dimethyl-cyclohex-3-enecarboxylic acid chloride.

Example 3

LC/MS=403 (M⁺+1)

Retention time: 2.46 min

LC: Thermo Electron Surveyor HPLC

MS: Finnigan LCQ Advantage MAX Mass Spectrometer

Column: Phenomenex Polar RP 30 mm×4.6 mm

Solvents: Acetonitrile with 0.1% formic acid, Water with 0.1% formic acid

Gradient: 0 min-0.1 min 5% ACN, 0.1 min-1.95 min 5%-100% ACN, 1.95 min-3.5 min 100% ACN, 3.5 min-3.55 min 100%-5% ACN, 3.55 min-4 min 5% ACN.

Example 4

LC/MS=403 (M⁺+1)

Retention time: 2.54 min

LC: Thermo Electron Surveyor HPLC

MS: Finnigan LCQ Advantage MAX Mass Spectrometer

Column: Phenomenex Polar RP 30 mm×4.6 mm

Solvents: Acetonitrile with 0.1% formic acid, Water with 0.1% formic acid

Gradient: 0 min-0.1 min 5% ACN, 0.1 min-1.95 min 5%-100% ACN, 1.95 min-3.5 min 100% ACN, 3.5 min-3.55 min 100%-5% ACN, 3.55 min-4 min 5% ACN.

Synthesis of (1S,6S)-4,6-dimethyl-cyclohex-3-enecarboxylic acid chloride

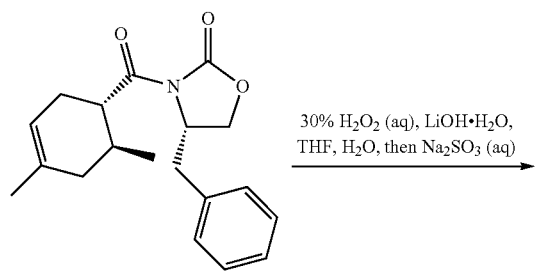

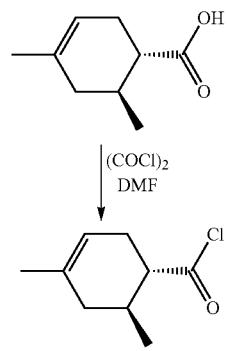

4S-benzyl-3-(4,6S-dimethyl-cyclohex-3-ene-1S-carbonyl)-oxazolidin-2-one, prepared in a method similar to that described in *J. Am. Chem. Soc.* 110(4), 1988, 1238-1256, was dissolved in THF (1000 mL) and H₂O (350 mL). The solution was cooled in an ice bath and 30% H₂O₂ (36 mL, 354 mmol) was slowly added followed by LiOH*H₂O (9.90 g, 263 mmol) in one portion. The reaction was allowed to slowly warm to rt and was stirred for 16 h. The reaction was then cooled in an ice bath. Na₂SO₃ (60 g, 472 mmol) was dissolved H₂O (400 mL) and added very slowly to the cooled reaction mixture. The solution was stirred for 1 h, and the layers were separated. The organics were removed under reduced pressure. The aqueous was added back to the organics concentrate and the mixture was extracted with CH₂Cl₂ (2×50 mL). The pH of the aqueous phase was adjusted to 2 by slow addition of concentrated aqueous HCl. The aqueous was extracted with EtOAc (4×300 mL) and the combined extracts were dried over Na₂SO₄. Removal of organics under reduced pressure and co-evaporation with hexanes afforded (1S,6S)-4,6-dimethyl-cyclohex-3-enecarboxylic acid (14.14 g, 78%) as a white solid.

4,6-S-dimethyl-cyclohex-3-ene-1S-carboxylic acid (944 mg, 6.17 mmol) was dissolved in CH₂Cl₂ (10 mL) and DMF (20 µL) was added. The solution was cooled to 0° C. and then (COCl)₂ (700 µL, 7.38 mmol) was slowly added. The reaction was stirred in an ice bath for 1 hour and then concentrated. The residue was taken up in hexanes and concentrated; this hexanes coevaporation was repeated once more. The resulting acid chloride was used without further purification.

Example 5

(S)-5-(3,3-Dimethylbut-1-ynyl)-3-(N-isopropyl-4-methylcyclohex-3-enecarboxamido)thiophene-2-carboxylic acid

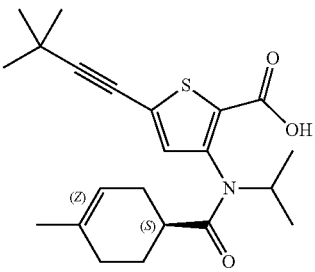

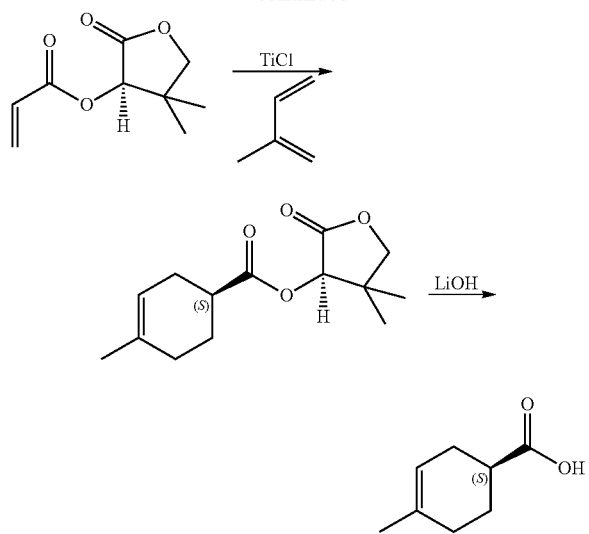

Acrylic acid 4,4-dimethyl-2-oxo-tetrahydro-furan-3-yl ester (R) (2.92 g, 15.9 mmol) in dichloromethane (20 mL) and hexanes (3 mL) was cooled to −10° C. and treated with titanium tetrachloride (2.4 mL, 2.4 M in dichloromethane, 2.4 mmol). The red solution was stirred for 15 min and treated with isoprene (2.4 mL, 23.8 mmol) dropwise over 5 min. After stirring for 1.5 h, an additional portion of isoprene (2.4 mL, 23.8 mmol) was added and the reaction mixture was stirred at −10 to 0° C. for 2.5 h. After cooling to −10° C., the reaction mixture was quenched with ammonium chloride (sat. aq.). Water and ethyl acetate:hexanes (1:1) were added. The organic layer was separated and the aqueous layer was extracted again with ethyl acetate:hexanes (1:1). The combined organic layers were dried over sodium sulfate, filtered and concentrated. The residue was purified by flash chromatography (10-40% EtOAc:Hex, 80 g column) to afford 3.35 g (84% yield) of 4-methyl-cyclohex-3-(S)-enecarboxylic acid 4,4-dimethyl-2-oxo-tetrahydro-furan-3-yl ester as a clear oil.

4-Methyl-cyclohex-3-(S)-enecarboxylic acid 4,4-dimethyl-2-oxo-tetrahydro-furan-3-yl ester (3.34 g, 13.2 mmol) in THF (25 mL), water (2.5 mL) and methanol (2.5 mL) was treated with lithium hydroxide monohydrate (2.8 g, 66.2 mmol) and warmed to 50° C. with stirring. After 1 h, the reaction mixture treated with 1M HCl (about 25 mL). The mixture was extracted with hexanes:ethyl acetate (200 mL: 15 mL), dried over sodium sulfate, filtered and concentrated to 2.4 g of a white semi-solid. The residue was redissolved in hexanes:dichloromethane (100 mL, 95:5), washed with water, dried over sodium sulfate, filtered and concentrated to 1.68 g (91% yield) of 4-methyl-cyclohex-3-enecarboxylic acid (S) as a white powder.

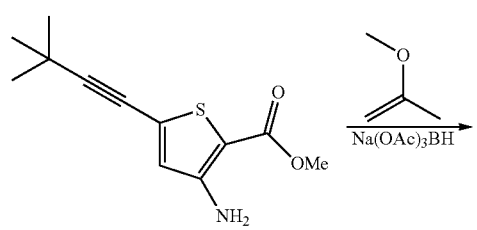

Methyl 3-amino-5-(3,3-dimethylbut-1-ynyl)thiophene-2-carboxylate (see WO 2008058393) (12.0 g, 50.6 mmol) in dichloromethane (150 mL) was placed in a cool water bath (12 deg C.) and treated dropwise with 2-methoxyprop-1-ene (14.6 mL, 152 mmol) over about 6 minutes followed by acetic acid (8.7 mL) over about 5 minutes. Sodium triacetoxyborohydride (16.1 g, 152 mmol) was added portionwise over about 30 minutes. The reaction mixture was allowed to warm to ambient temperature and was stirred for 16 h. The resulting light orange solution was poured into cold sodium bicarbonate (sat aq, 200 mL). The organic layer was separated and the aqueous layer was extracted twice with dichloromethane (150 mL each). The combined organic layers were washed with sodium bicarbonate (sat aq) and brine, dried over sodium sulfate (anhyd), filtered and concentrated to an orange oil. Silica gel chromatography (0-15% EtOAc:Hex) afforded 13.0 g (92% yield) of the desired methyl 5-(3,3-dimethylbut-1-ynyl)-3-(isopropylamino)thiophene-2-carboxylate as a light yellow oil which solidified upon standing to a waxy crystalline solid, and was used in the subsequent step.

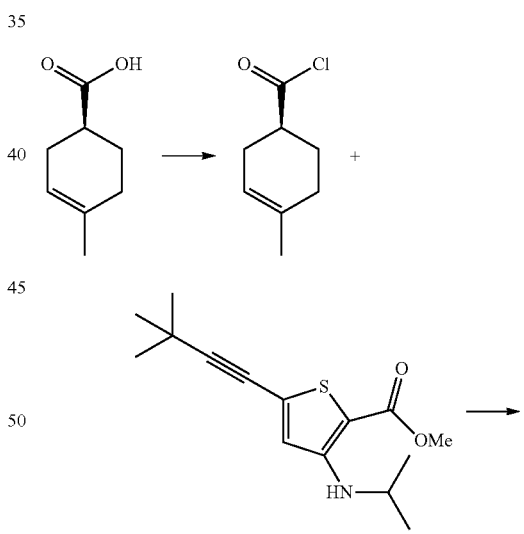

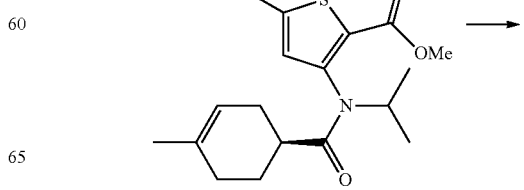

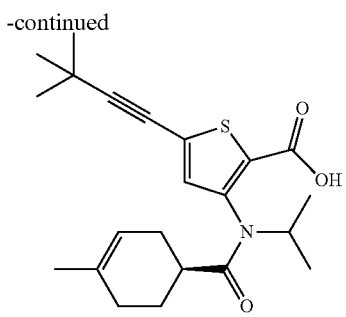

4-Methyl-cyclohex-3-enecarboxylic acid (S) (100 mg, 0.71 mmol), azeotropically dried by evaporation from toluene, was treated with potassium phosphate tribasic (303 mg, 2.1 mmol), suspended in dichloromethane (2 mL) and treated with dimethylformamide (1 drop). The reaction mixture was cooled to 0° C. and treated dropwise with oxalyl chloride (0.2 mL, 1.4 mmol). The reaction mixture was allowed to warm to ambient temperature while stirring for 2 h. After filtering the solids, the solution was concentrated, treated with hexanes and concentrated again to afford 4-methyl-cyclohex-3-enecarbonyl chloride (S) as a light yellow oil which was used immediately in the next step.

4-Methyl-cyclohex-3-enecarbonyl chloride (S) (0.71 mmol), methyl 5-(3,3-dimethylbut-1-ynyl)-3-(isopropylamino)thiophene-2-carboxylate (80 mg, 0.29 mmol) and potassium phosphate tribasic (152 mg, 0.71 mmol) were suspended in dichloroethane (0.75 mL), sealed with a cap and heated to 90° C. After 16 h, the reaction mixture was cooled and partitioned between ethyl acetate and water. The organic layer was separated and the aqueous extracted again with ethyl acetate. The combined organic layers were dried over sodium sulfate, filtered and concentrated. Flash chromatography (10-35% EtOAc:Hexanes) afforded 59 mg (51% yield) of the desired (S)-methyl 5-(3,3-dimethylbut-1-ynyl)-3-(N-isopropyl-4-methylcyclohex-3-enecarboxamido)thiophene-2-carboxylate as a white foam.

(S)-Methyl 5-(3,3-dimethylbut-1-ynyl)-3-(N-isopropyl-4-methylcyclohex-3-enecarboxamido)thiophene-2-carboxylate (123 mg, 0.31 mmol) was dissolved in THF (2 mL). Water (0.5 mL), methanol (0.5 mL) and lithium hydroxide (129 mg, 3.1 mmol) were added. The mixture was sealed and heated to 45 deg C. for 30 min. After an additional 1 h at ambient temperature, the mixture was treated with 10% HCl (until the pH was less than 3) and partitioned between water and ethyl acetate. The organic layer was separated, dried over sodium sulfate (anhyd) and the residue was purified by reverse phase HPLC to give the title compound, 41 mg (35% yield): MS (m/z): 388.0 [M+H]+; HPLC retention time 4.59 min (2-98% acetonitrile: water with 0.05% trifluoroacetic acid).

Example 6

(R)-5-(3,3-Dimethylbut-1-ynyl)-3-(N-isopropyl-4-methylcyclohex-3-enecarboxamido)thiophene-2-carboxylic acid

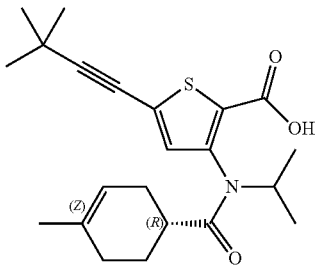

The title compound was prepared in a manner similar to Example 5 using acrylic acid 4,4-dimethyl-2-oxo-tetrahydro-furan-3-yl ester (S) in place of acrylic acid 4,4-dimethyl-2-oxo-tetrahydro-furan-3-yl ester (R): MS (m/z): 388.0 [M+H]+; HPLC retention time 4.59 min (2-98% acetonitrile: water with 0.05% trifluoroacetic acid).

Acrylic acid 4,4-dimethyl-2-oxo-tetrahydro-furan-3-yl ester (R) was prepared in the following manner: a solution of 3-(S)-hydroxy-4,4-dimethyl-dihydro-furan-2-one (2.60 g, mmol) and diisopropylethylamine (5.2 mL, 30 mmol) in dichloromethane (25 mL) was cooled to −10° C., treated dropwise with acryloyl chloride (2.03 mL, 25 mmol) and stirred for 2 h. 1M HCl (20 mL) was added and the organic layer was washed with sodium bicarbonate and water. The organic layer was dried over sodium sulfate, filtered and concentrated. Flash chromatography (10-40% EtOAc, hexanes) afforded 2.09 g (57% yield) of the desired acrylic acid 4,4-dimethyl-2-oxo-tetrahydro-furan-3-yl ester (R) as a clear oil.

Example 7

5-(3,3-Dimethylbut-1-ynyl)-3-((1S,6S)—N-((1r,4S)-4-hydroxycyclohexyl)-4,6-dimethylcyclohex-3-enecarboxamido)thiophene-2-carboxylic acid

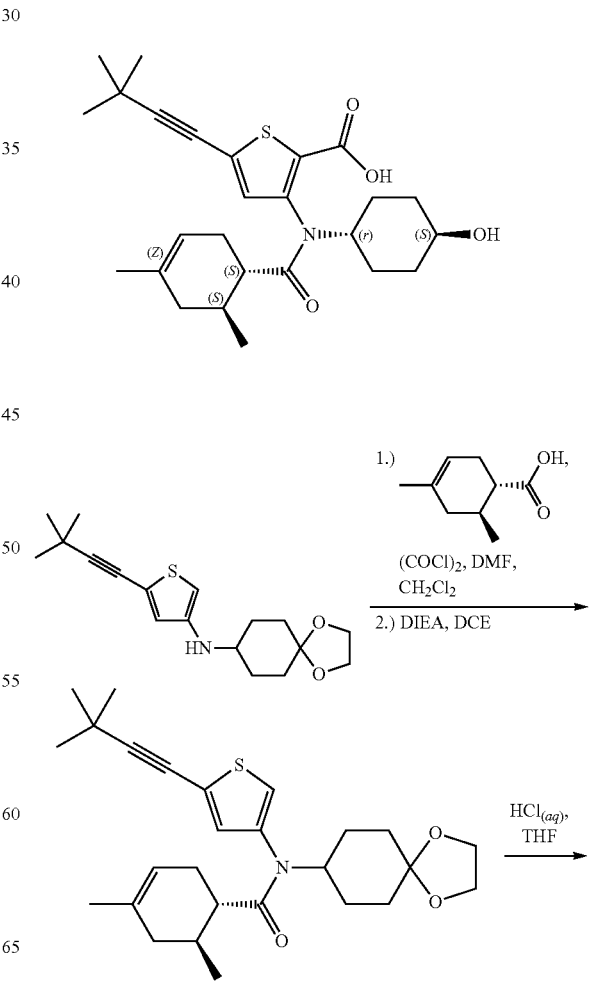

-continued

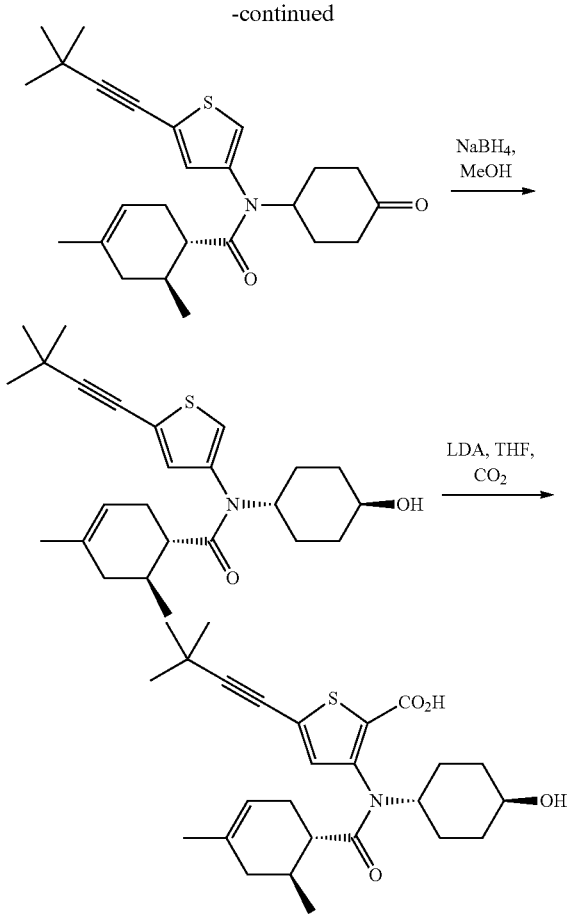

(1S,6S)-4,6-Dimethyl-cyclohex-3-ene-carboxylic acid (3.04 g, 19.7 mmol) was dissolved in CH$_2$Cl$_2$ (30 mL) and DMF (20 μL) was added. The solution was cooled to 0° C. and then (COCl)$_2$ (3.7 mL, 39 mmol) was added slowly. The reaction was stirred in an ice bath for 2 hours and then concentrated. The residue was taken up in hexanes and concentrated; this hexanes coevaporation was repeated once more. To the residue was added [5-(3,3-dimethyl-but-1-ynyl)-thiophen-3-yl]-(1,4-dioxa-spiro[4.5]dec-8-yl)-amine (4.16 g, 13 mmol), diisopropylethylamine (4.5 mL, 26 mmol), and 1,2-dichloroethane (40 mL) at 0° C. The solution was warmed to room temperature and stirred overnight. The reaction was diluted with CH$_2$Cl$_2$, twice washed with saturated NH$_4$Cl (aq), dried over MgSO$_4$, filtered, concentrated, and purified by silica gel column chromatography, eluting with a mixture of 0-75% EtOAc/hexanes, to give (1S,6S)-4,6-dimethyl-cyclohex-3-ene-carboxylic acid [5-(3,3-dimethyl-but-1-ynyl)-thiophen-3-yl]-(1,4-dioxa-spiro[4.5]dec-8-yl)-amide (5.6 g, 12 mmol) as a single isomer.

(1S,6S)-4,6-Dimethyl-cyclohex-3-ene-carboxylic acid [5-(3,3-dimethyl-but-1-ynyl)-thiophen-3-yl]-(1,4-dioxa-spiro[4.5]dec-8-yl)-amide (5.6 g, 12 mmol) was dissolved in THF (70 mL) and treated with 4M HCl (35 mL). The reaction mixture was heated to 45° C. and stirred for 2.5 h. THF was removed in vacuo, and the aqueous layer was thrice extracted into ethyl acetate. The combined organic layers were washed with saturated NaHCO$_3$ (aq), water, and brine, dried over MgSO$_4$, filtered, and concentrated to give (1S,6S)-4,6-dimethyl-cyclohex-3-ene-carboxylic acid [5-(3,3-dimethyl-but-1-ynyl)-thiophen-3-yl]-(4-oxo-cyclohexyl)-amide (5.05 g, 12 mmol).

(1S,6S)-4,6-Dimethyl-cyclohex-3-ene-carboxylic acid [5-(3,3-dimethyl-but-1-ynyl)-thiophen-3-yl]-(4-oxo-cyclohexyl)-amide (2.0 g, 4.9 mmol) in MeOH (100 mL) was treated with sodium borohydride (230 mg, 6.0 mmol) at 0° C. After stirring for 30 min, 4M HCl (6 mL) was added and the reaction mixture was twice extracted with ethyl acetate. The combined organic layers washed with saturated NaHCO$_3$ (aq), brine, dried over MgSO$_4$, filtered, and concentrated. Silica gel chromatography (20-60% ethyl acetate/hexanes) gave the desired (1S,6S)-4,6-dimethyl-cyclohex-3-ene-carboxylic acid [5-(3,3-dimethyl-but-1-ynyl)-thiophen-3-yl]-(trans-4-hydroxy-cyclohexyl)-amide (1.74 g, 4.2 mmol).

(1S,6S)-4,6-Dimethyl-cyclohex-3-ene-carboxylic acid [5-(3,3-dimethyl-but-1-ynyl)-thiophen-3-yl]-(trans-4-hydroxy-cyclohexyl)-amide (1.74 g, 4.2 mmol) in THF (50 mL) was cooled to −78° C. and treated with lithium diisopropylamine (8.4 mL, 2.0M in heptane/THF/PhEt, 16.8 mmol) and allowed to warm to 0° C. over the course of 2 hours. CO$_2$ was vigorously bubbled through the reaction solution for 10 minutes. The reaction was then quenched with the addition of iPrOH, diluted with ethyl acetate, washed with saturated NH$_4$Cl (aq), dried over MgSO$_4$, filtered, and concentrated. Silica gel chromatography (0-100% ethyl acetate/dichloromethane) afforded 530 mg (1.2 mmol) of the title compound: MS (m/z): 458.1 [M+H]+; HPLC retention time (Gemini column) 4.35 min (2-98% acetonitrile: water with 0.05% trifluoroacetic acid).

Example 8

5-(3,3-Dimethylbut-1-ynyl)-3-((R)—N-((1r,4R)-4-hydroxycyclohexyl)-4-methylcyclohex-3-enecarboxamido)thiophene-2-carboxylic acid

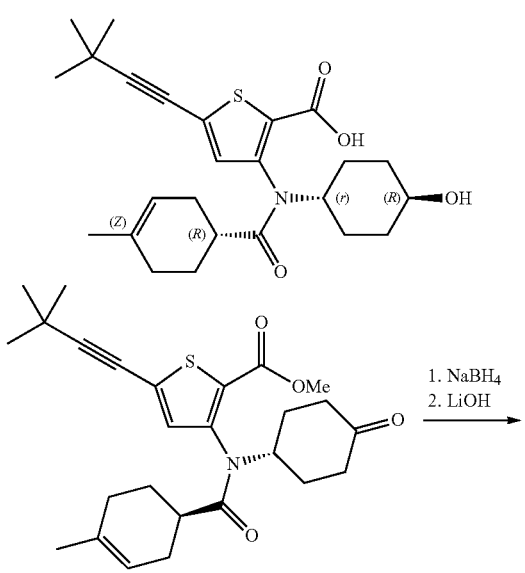

-continued

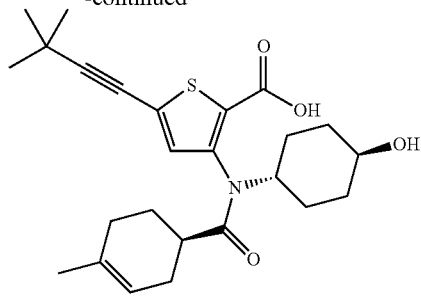

(R)-Methyl 5-(3,3-dimethylbut-1-ynyl)-3-(4-methyl-N-(4-oxocyclohexyl)cyclohex-3-enecarboxamido)thiophene-2-carboxylate (see U.S. Ser. No. 11/21335) (250 mg, 0.55 mmol) was dissolved in a mixture of tetrahydrofuran (4 mL) and water (0.4 mL), cooled to 0 deg C. and treated with sodium borohydride (21 mg, 0.55 mmol). After stirring for 30 min, the mixture was treated dropwise with 10% aq HCl (4 mL) and stirred an additional 15 min. Water (10 mL) was added, and the mixture was extracted twice with ethyl acetate, dried and concentrated to afford the desired methyl 5-(3,3-dimethylbut-1-ynyl)-3-((R)—N-((1r,4R)-4-hydroxycyclohexyl)-4-methylcyclohex-3-enecarboxamido)thiophene-2-carboxylate, which was taken on crude to the next step.

Methyl 5-(3,3-dimethylbut-1-ynyl)-3-((R)—N-((1r,4R)-4-hydroxycyclohexyl)-4-methylcyclohex-3-enecarboxamido)thiophene-2-carboxylate (0.55 mmol) was dissolved in THF (4 mL). Water (1 mL), methanol (1 mL) and lithium hydroxide (234 mg, 5.6 mmol) were added. The mixture was sealed and heated to 45 deg C. for 30 min. After an additional 1 h at ambient temperature, the mixture was treated with 10% HCl (until the pH was less than 3) and partitioned between water and ethyl acetate. The organic layer was separated, dried over sodium sulfate (anhyd) and the residue was purified by reverse phase HPLC to give the title compound, 50 mg (20% yield): MS (m/z): 444.0 [M+H]+; HPLC retention time 4.15 min (2-98% acetonitrile: water with 0.05% trifluoroacetic acid).

COMPARATIVE EXAMPLES

Comparative Example 1

5-(3,3-Dimethylbut-1-ynyl)-3-((1r,4r)-N-isopropyl-4-methylcyclohexanecarboxamido)thiophene-2-carboxylic acid

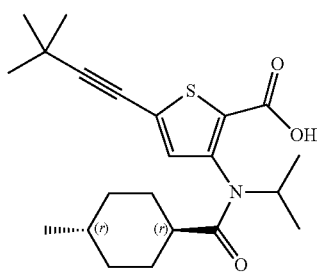

The synthesis of the title compound is described in WO 2006/072347 (Example 1).

Comparative Example 2

5-(3,3-Dimethylbut-1-ynyl)-3-((1r,4R)—N-((1r,4R)-4-hydroxycyclohexyl)-4-methylcyclohexanecarboxamido)thiophene-2-carboxylic acid

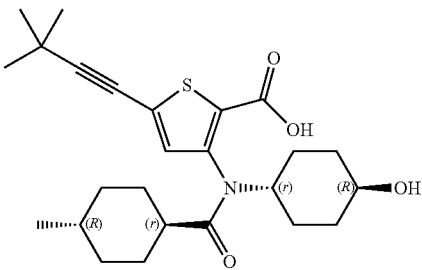

The synthesis of the title compound is described in WO08/58393 (example 1).

Comparative Example 3

5-(3,3-Dimethylbut-1-ynyl)-3-((1S,2S,4S)—N-isopropyl-2,4-dimethylcyclohexanecarboxamido)thiophene-2-carboxylic acid

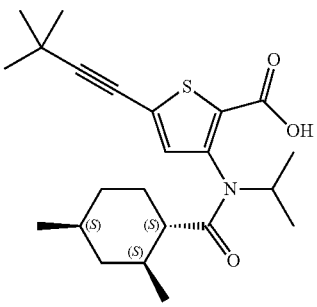

Synthesis of
(1S,2S,4S)-2,4-dimethylcyclohexanecarboxylic acid

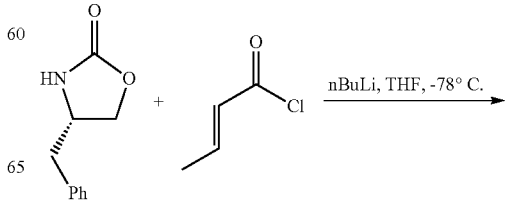

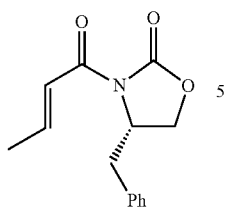

(S)-4-Benzyloxazolidin-2-one (35 g, 0.2 mol) was dissolved in THF (500 mL) and cooled to −78° C. A solution of nBuLi in hexane (80 mL, 0.2 mol) was added dropwise. The solution was stirred at this temperature for 30 min and then (E)-but-2-enoyl chloride (19 mL, 0.2 mol) was added slowly. The cold bath was removed and the reaction was allowed to stir at room temperature for 1 h, whereupon saturated NH$_4$Cl solution (200 mL) was added. Most of the THF was removed under vacuum and the mixture was partitioned between ether and brine. After drying over Na$_2$SO$_4$, the organic layer was concentrated and the residue purified by silica gel chromatography (20% EtOAc in hexanes) to give the desired product (39 g, 79% yield) as a white solid.

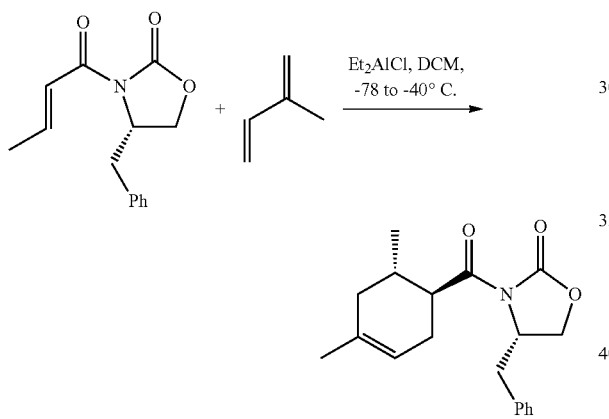

A solution of (S,E)-4-benzyl-3-but-2-enoyloxazolidin-2-one (34.5 g, 0.14 mol) and isoprene (250 mL) in DCM was cooled to −78° C. To this solution was added a solution of Et$_2$AlCl in toluene (100 mL, 0.18 mol) dropwise. The solution was warmed to −40° C. and stirred at this temperature overnight. 2 N HCl solution (150 mL) was added. Most of the DCM was removed under vacuum and the mixture was extracted with ether. After drying over Na$_2$SO$_4$, the combined organic layer was concentrated and the residue purified by silica gel chromatography (0-30% EtOAc in hexanes) to give the desired product (39 g, 88% yield) as a crystalline white solid.

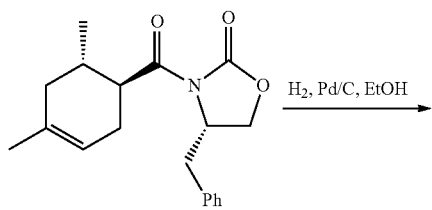

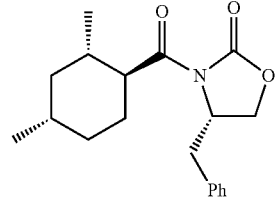

A mixture of (S)-4-benzyl-3-((1S,6S)-4,6-dimethylcyclohex-3-enecarbonyl)oxazolidin-2-one (6 g, 19.1 mmol) and 10% Pd/C (500 mg) in EtOH (50 mL) under a H$_2$ atmosphere (1 atm) was stirred at room temperature overnight. The reaction mixture was filtered through a pad of diatomaceous earth and concentrated to give a 3:1 mixture of diastereomers, which were separated by preparative chiral column chromatography (Chiralcel OD-H (20 cm×250 cm; semi prep): Retention time: 24 min, 33 min (major) (80:20 heptane:ethanol)), providing (S)-4-benzyl-3-((1S,2S,4S)-2,4-dimethylcyclohexanecarbonyl)oxazolidin-2-one (2.3 g, 38%).

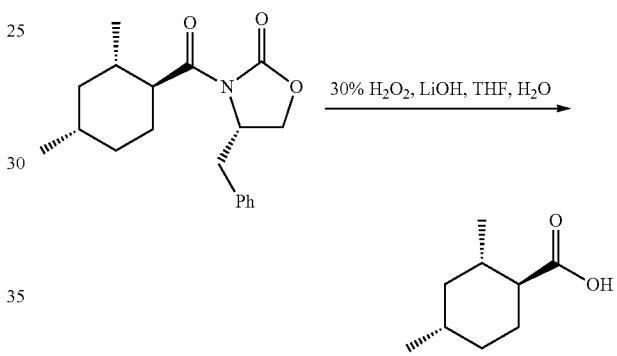

At 0° C., to a solution of (S)-4-benzyl-3-((1S,2S,4S)-2,4-dimethylcyclohexanecarbonyl)oxazolidin-2-one (1.5 g, 4.75 mmol) in THF (30 mL) and water (10 L) was added 30% H$_2$O$_2$ (3.7 mL) dropwise followed by addition of lithium hydroxide monohydrate (0.4 g, 9.5 mmol) in one portion. The resulting solution was stirred at room temperature overnight. Na$_2$SO$_3$ (6 g) in water (20 mL) was added slowly at 0° C., followed by saturated NaHCO$_3$ (15 mL). THF was removed in vacuo. The residue was extracted with DCM (2×25 mL). The combined extracts were back extracted with saturated NaHCO$_3$ (25 mL). The pH of the combined aqueous phases was adjusted to pH=1 with concentrated HCl. The aqueous mixture was then extracted with EtOAc (5×mL), dried over Na$_2$SO$_4$, and concentrated to give crude product (0.76 g) as a white solid, which was used without further purification.

Synthesis of 5-(3,3-dimethylbut-1-ynyl)-3-((1S,2S, 4S)—N-isopropyl-2,4-dimethylcyclohexanecarboxamido)thiophene-2-carboxylic acid

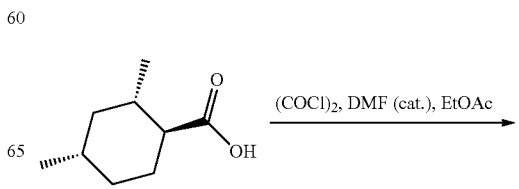

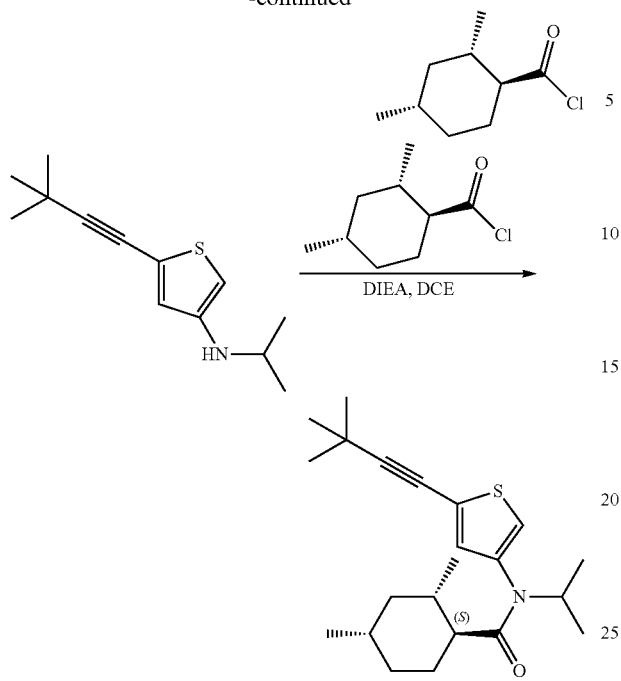

To a solution of carboxylic acid (200 mg, 1.3 mmol) and DMF (1 drop) in EtOAc (5 mL) was added oxalyl chloride (0.3 mL, 3.45 mmol) at room temperature. The reaction was stirred for 2 h and the volatiles were removed in vacuo. A solution of 5-(3,3-dimethylbut-1-ynyl)-N-isopropylthiophen-3-amine (170 mg, 0.77 mmol) and DIEA (0.3 mL) in DCE (1 mL) was then added. The reaction was stirred overnight. The mixture was poured into EtOAc (150 mL), and the organics were washed with saturated NaHCO₃ (2×50 mL) and brine (50 mL). After drying over Na₂SO₄, the organic layer was concentrated and the residue purified by silica gel chromatography (0-20% EtOAc in hexanes) to give the desired product (116 mg, 25% yield) as a dark oil.

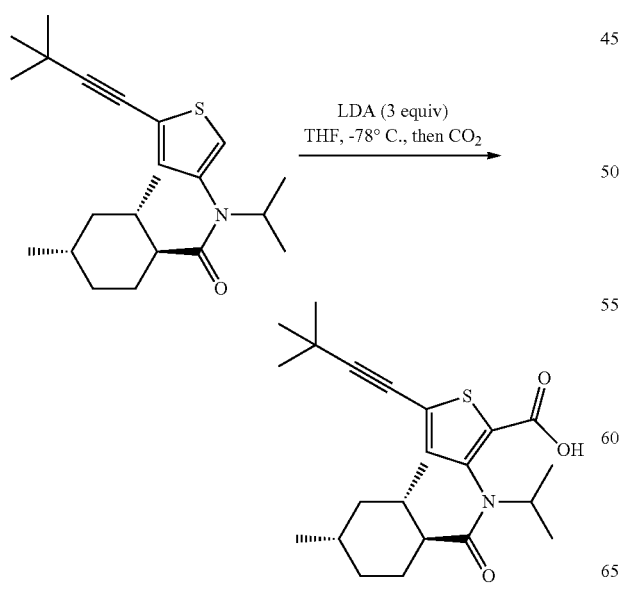

The amide from the previous step (116 mg, 0.32 mmol, 1.0 equiv) was dissolved in THF (5 mL) in a 50 mL two-necked round-bottomed flask. The solution was cooled to −78° C. in an acetone-dry ice bath. To this solution, LDA (0.5 mL, 0.96 mmol, 3.0 equiv) was added dropwise via a syringe while maintained internal temperature lower than −70° C. After addition, the solution was stirred at −78° C. for 2 h. CO₂ was bubbled into solution for 3 min. 1.0 mL IPA was added to reaction followed by 30 mL 10% citric acid. The mixture was poured into EtOAc (100 mL) and organics were washed with 10% citric acid (2×30 mL) and brine (100 mL). After drying over Na₂SO₄ and concentrated to dryness in vacuo, the residue was purified by reverse phase HPLC to yield the product (45 mg, 34% yield). MS (m/z): 404.5 [M+H]+; HPLC retention time 5.18 min (2-98% acetonitrile:water with 0.05% trifluoroacetic acid).

Comparative Example 4

5-(3,3-Dimethylbut-1-ynyl)-3-((1R,2R,4R)—N-isopropyl-2,4-dimethylcyclohexanecarboxamido) thiophene-2-carboxylic acid

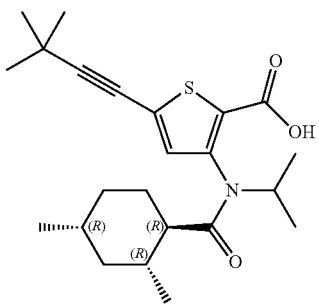

5-(3,3-Dimethylbut-1-ynyl)-3-((1R,2R,4R)—N-isopropyl-2,4-dimethyl-cyclohexanecarboxamido)thiophene-2-carboxylic acid was prepared in a similar fashion as Example 27 except that (1R,2R,4R)-2,4-dimethylcyclohexanecarboxylic acid was used instead of (1S,2S,4S)-2,4-dimethylcyclohexanecarboxylic acid. MS (m/z): 404.0 [M+H]⁺; HPLC retention time 8.75 min (2-98% acetonitrile: water with 0.05% trifluoroacetic acid).

Synthesis of (1R,2R,4R)-2,4-dimethylcyclohexanecarboxylic acid

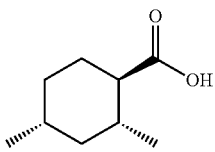

A mixture of (R)-4-benzyl-3-((1R,6R)-4,6-dimethylcyclohex-3-ene-carbonyl)oxazolidin-2-one (1.5 g, 4.8 mmol) (*J. Am. Chem. Soc.* 110(4), 1988, 1238-1256) in EtOH (24 mL) and 10% Pd/C (500 mg) was stirred under a $H_2$ atmosphere (1 atm) at room temperature overnight. The reaction mixture was filtered through a pad of diatomaceous earth and concentrated to give a 3:1 mixture of diastereomers which were separated by preparative chiral column chromatography: Chiral-Pak AD-H (20 cm×250 cm; semi prep): Retention time: 5.11 min, 6.25 min (80:20 heptane:ethanol), providing the desired compound (R)-4-benzyl-3-((1R,2R,4R)-2,4-dimethylcyclohexanecarbonyl)oxazolidin-2-one (0.65 g).

A solution of (R)-4-benzyl-3-((1R,2R,4R)-2,4-dimethylcyclohexanecarbonyl) oxazolidin-2-one (0.65 g, 2.0 mmol) in THF/water (3:1, 20 mL) was cooled in an ice bath and 30% $H_2O_2$ (1 mL, 16.5 mmol) was slowly added, followed by LiOH*H2O(s) (0.17 g, 4.0 mmol) in one portion. The reaction was allowed to slowly warm to room temperature and stirred for 16 h. The reaction was then cooled in an ice bath. A 1 M solution of $Na_2SO_3$ was very slowly added to the cooled reaction mixture. The solution was stirred for 1 h, and the layers were separated. The organics were removed under reduced pressure. The aqueous was added back to the organics concentrate and was washed with $CH_2Cl_2$ (2×50 mL). The pH of the aqueous solution was adjusted to 2 through slow addition of concentrated hydrochloric acid. The resulting mixture was extracted with EtOAc (1×50 mL) and dried over $Na_2SO_4$. Solvents were removed under reduced pressure, co-evaporating with hexanes, to afford 0.300 g of (1R,2R,4R)-2,4-dimethylcyclohexanecarboxylic acid as a white solid.

BIOLOGICAL EXAMPLES

Antiviral Activity

Another aspect of the invention relates to methods of inhibiting viral infections, comprising the step of treating a sample or subject suspected of needing such inhibition with a composition of the invention.

Within the context of the invention samples suspected of containing a virus include natural or man-made materials such as living organisms; tissue or cell cultures; biological samples such as biological material samples (blood, serum, urine, cerebrospinal fluid, tears, sputum, saliva, tissue samples, and the like); laboratory samples; food, water, or air samples; bioproduct samples such as extracts of cells, particularly recombinant cells synthesizing a desired glycoprotein; and the like. Typically the sample will be suspected of containing an organism which induces a viral infection, frequently a pathogenic organism such as a tumor virus. Samples can be contained in any medium including water and organic solvent\water mixtures. Samples include living organisms such as humans, and man made materials such as cell cultures.

If desired, the anti-virus activity of a compound of the invention after application of the composition can be observed by any method including direct and indirect methods of detecting such activity. Quantitative, qualitative, and semiquantitative methods of determining such activity are all contemplated. Typically one of the screening methods described above are applied, however, any other method such as observation of the physiological properties of a living organism are also applicable.

The antiviral activity of a compound of the invention can be measured using standard screening protocols that are known. For example, the antiviral activity of a compound can be measured using the following general protocols.

Cell-Based Flavivirus Immunodetection Assay

BHK21 or A549 cells are trypsinized, counted and diluted to $2\times10^5$ cells/mL in Hams F-12 media (A549 cells) or RPMI-1640 media (BHK21 cells) supplemented with 2% fetal bovine serum (FBS) and 1% penicillin/streptomycin. $2\times10^4$ cells are dispensed in a clear 96-well tissue culture plates per well and placed at 37° C., 5% $CO_2$ overnight. On the next day, the cells are infected with viruses at multiplicity of infection (MOI) of 0.3 in the presence of varied concentrations of test compounds for 1 hour at 37° C. and 5% $CO_2$ for another 48 hours. The cells are washed once with PBS and fixed with cold methanol for 10 min. After washing twice with PBS, the fixed cells are blocked with PBS containing 1% FBS and 0.05% Tween-20 for 1 hour at room temperature. The primary antibody solution (4G2) is then added at a concentration of 1:20 to 1:100 in PBS containing 1% FBS and 0.05% Tween-20 for 3 hours. The cells are then washed three times with PBS followed by one hour incubation with horseradish peroxidase (HRP)-conjugated anti-mouse IgG (Sigma, 1:2000 dilution). After washing three times with PBS, 50 microliters of 3,3',5,5'-tetramethylbenzidine (TMB) substrate solution (Sigma) is added to each well for two minutes. The reaction is stopped by addition of 0.5 M sulfuric acid. The plates are read at 450 nm absorbance for viral load quantification. After measurement, the cells are washed three times with PBS followed by incubation with propidium iodide for 5 min. The plate is read in a Tecan Safire™ reader (excitation 537 nm, emission 617 nm) for cell number quantification. Dose response curves are plotted from the mean absorbance versus the log of the concentration of test compounds. The $EC_{50}$ is calculated by non-linear regression analysis. A positive control such as N-nonyl-deoxynojirimycin may be used.

Cell-Based Flavivirus Cytopathic Effect Assay

For testing against West Nile virus or Japanese encephalitis virus, BHK21 cells are trypsinized and diluted to a concentration of $4\times10^5$ cells/mL in RPMI-1640 media supplemented with 2% FBS and 1% penicillin/streptomycin. For testing against dengue virus, Huh7 cells are trypsinized and diluted to a concentration of $4\times10^5$ cells/mL in DMEM media supplemented with 5% FBS and 1% penicillin/streptomycin. A 50 microliter of cell suspension ($2\times10^4$ cells) is dispensed per well in a 96-well optical bottom PIT polymer-based plates (Nunc). Cells are grown overnight in culture medium at 37° C., 5% $CO_2$, and then infected with West Nile virus (e.g. B956 strain) or Japanese encephalitis virus (e.g. Nakayama strain) at MOI=0.3, or with dengue virus (e.g. DEN-2 NGC strain) at MOI=1, in the presence of different concentrations of test compounds. The plates containing the virus and the compounds are further incubated at 37° C., 5% $CO_2$ for 72 hours. At the end of incubation, 100 microliters of CellTiter-Glo™ reagent is added into each well. Contents are mixed for 2 minutes on an orbital shaker to induce cell lysis. The plates are incubated at room temperature for 10 minutes to stabilize luminescent signal. Luminescence reading is recorded using a plate reader. A positive control such as N-nonyl-deoxynojirimycin may be used.

Antiviral Activity in a Mouse Model of Dengue Infection.

Compounds are tested in vivo in a mouse model of dengue virus infection (Schul et al. J. Infectious Dis. 2007; 195:665-74). Six to ten week old AG129 mice (B&K Universal Ltd, HII, UK) are housed in individually ventilated cages. Mice are injected intraperitoneally with 0.4 mL TSV01 dengue virus 2 suspension. Blood samples are taken by retro orbital puncture under isoflurane anaesthesia. Blood samples are collected in tubes containing sodium citrate to a final concentration of 0.4%, and immediately centrifuged for 3 minutes at 6000 g to obtain plasma. Plasma (20 microliters) is diluted in 780 microliters RPMI-1640 medium and snap frozen in liquid nitrogen for plaque assay analysis. The remaining plasma is reserved for cytokine and NS1 protein level determination. Mice develop dengue viremia rising over several days, peaking on day 3 post-infection.

For testing of antiviral activity, a compound of the invention is dissolved in vehicle fluid, e.g. 10% ethanol, 30% PEG 300 and 60% D5W (5% dextrose in water; or 6N HCl (1.5 eq):1N NaOH (pH adjusted to 3.5): 100 mM citrate buffer pH 3.5 (0.9% v/v:2.5% v/v: 96.6% v/v). Thirty six 6-10 week old AG129 mice are divided into six groups of six mice each. All mice are infected with dengue virus as described above (day 0). Group 1 is dosed by oral gavage of 200 mL/mouse with 0.2 mg/kg of a compound of the invention twice a day (once early in the morning and once late in the afternoon) for three consecutive days starting on day 0 (first dose just before dengue infection). Groups 2, 3 and 4 are dosed the same way with 1 mg/kg, 5 mg/kg and 25 mg/kg of the compound, respectively. A positive control may be used, such as (2R,3R,4R,5R)-2-(2-amino-6-hydroxy-purin-9-yl)-5-hydroxymethyl-3-methyl-tetrahydro-furan-3,4-diol, dosed by oral gavage of 200 microliters/mouse the same way as the previous groups. A further group is treated with only vehicle fluid.

On day 3 post-infection approximately 100 microliter blood samples (anti-coagulated with sodium citrate) are taken from the mice by retro-orbital puncture under isoflurane anaesthesia. Plasma is obtained from each blood sample by centrifugation and snap frozen in liquid nitrogen for plague assay analysis. The collected plasma samples are analyzed by plague assay as described in Schul et al. Cytokines are also analysed as as described by Schul. NS1 protein levels are analysed using a Platelia™ kit (BioRad Laboratories). An anti-viral effect is indicated by a reduction in cytokine levels and/or NS1 protein levels.

Typically, reductions in viremia of about 5-100 fold, more typically 10-60 fold, most typically 20-30 fold, are obtained with 5-50 mg/kg bid dosages of the compounds of the invention.

HCV Assay Protocol

The anti-HCV activity of the compounds of this invention was tested in a human hepatoma Huh-7 cell line harboring a HCV replicon. The assay comprised the following steps:

Step 1: Compound Preparation and Serial Dilution.

Serial dilution was performed in 100% DMSO in a 384-well plate. A solution containing a compound at 225-fold concentration of the starting final serial dilution concentration was prepared in 100% DMSO and 15 µL added to the pre-specified wells in column 3 or 13 of a polypropylene 384-well plate. The rest of the 384-well plate was filled with 10 µL 100% DMSO except for columns 23 and 24, where 10 µL of 500 uM a HCV protease inhibitor (ITMN-191) in 100% DMSO was added. The HCV protease inhibitor was used a control of 100% inhibition of HCV replication. The plate was then placed on a Biomek FX Workstation to start the serial dilution. The serial dilution was performed for ten cycles of 3-fold dilution from column 3 to 12 or from column 13 to 22.

Step 2: Cell Culture Plate Preparation and Compound Addition

To each well of a black polypropylene 384-well plate, 90 µL of cell media containing 1600 suspended Huh-7 HCV replicon cells was added with a Biotek uFlow Workstation. A volume of 0.4 µL of the compound solution was transferred from the serial dilution plate to the cell culture plate on a Biomek FX Workstation. The DMSO concentration in the final assay condition was 0.44%. The plates were incubated for 3 days at 37° C. with 5% CO2 and 85% humidity.

Step 3: Detection of Cytotoxicity and Inhibition of Viral Replication a) Assessment of cytotoxicity: The media in the 384-well cell culture plate was aspirated with a Biotek EL405 plate-washer. A volume of 50 µL of a solution containing 400 nM Calcein AM in 100% PBS was added to each well of the plate with a Biotek uFlow Workstation. The plate was incubated for 30 minutes at room temperature before the fluorescence signal (emission 490 nm, exitation 520 nm) was measured with a Perkin Elmer Envision Plate Reader.

b) Assessment of inhibition of viral replication: The calcein-PBS solution in the 384-well cell culture plate was aspirated with a Biotek EL405 plate-washer. A volume of 20 µL of Dual-Glo luciferase buffer (Promega, Dual-Glo Luciferase Assay Reagent, cat. #E298B) was added to each well of the plate with a Biotek uFlow Workstation. The plate was incubated for 10 minutes at room temperature. A volume of 20 µL of a solution containing 1:100 mixture of Dual-Glo Stop & Glo substrate (Promega, Dual-Glo Luciferase Assay Reagent, cat. #E313B) and Dual-Glo Stop & Glo buffer (Promega, Dual-Glo Luciferase Assay Reagent, cat. #E314B) was then added to each well of the plate with a Biotek uFlow Workstation. The plate was incubated at room temperature for 10 minutes before the luminescence signal was measured with a Perkin Elmer Envision Plate Reader.

Step 4: Calculation

The percent cytotoxicity was determined by calcein AM conversion to fluorescent product. The average fluorescent signal from the DMSO control wells were defined as 100% nontoxic. The individual fluorescent signal from testing compound treated well was divided by the average signal from DMSO control wells and then multiplied by 100% to get the percent viability. The percent anti-HCV replication activity was determined by the luminescence signal from the testing well compared to DMSO controls wells. The background signal was determined by the average luminescence signal from the HCV protease inhibitor treated wells and was subtracted from the signal from the testing wells as well as the DMSO control wells. Following 3-fold serial dilutions, the $EC_{50}$ and $CC_{50}$ values were calculated by fitting % inhibition at each concentration to the following equation:

$$\% \text{ inhibition} = 100\% / [(EC_{50}/[I])^b + 1]$$

Where b is Hill's coefficient. See, for reference, Hill, A. V., *The Possible Effects of the Aggregation of the Molecules of Hemoglobin on its Dissociation Curves*, J. Physiol. 40: iv-vii. (1910).

% inhibition values at a specific concentration, for example 2 µM, can also be derived from the formula above.

When tested, certain compounds of this invention were found to inhibit viral replication as listed in Table 1:

TABLE 1

| Example | Wild-type $EC_{50}$ (nM) |
| --- | --- |
| 1 | 8 |
| 2 | 5 |
| 3 | 5 |
| 4 | 38 |
| 5 | 10 |
| 6 | 7 |
| 7 | <4.5 |
| 8 | <2.3 |
| Comparative example 1 | 26 |
| Comparative example 2 | 6 |
| Comparative example 3 | 50 |
| Comparative example 4 | 8 |

HCV Transient Transfection Assay Protocol

Cell Lines.

Huh-lunet, a Huh-7 clone that is highly permissive for HCV replication, was obtained from ReBLikon GmbH (Mainz, Germany). Huh-lunet cells were maintained in Dulbecco's Modified Eagle's Medium (DMEM; GIBCO, Carlsbad, Calif.) supplemented with 10% fetal bovine serum (FBS; Hyclone, Logan, Utah). Cells were maintained at 37° C. in humidified incubators (85% humidity) and under a 5% CO2 atmosphere.

Drug Susceptibility Determination Using Transient Transfection RepliconAssay.

PI-hRluc, a bicistronic replicon encoding the *Renilla luciferase* gene downstream of the polio IRES and the genotype 1b (Con-1 strain) HCV nonstructural genes (NS3-NS5B) downstream of the EMCV IRES, was used for transient transfection studies. The plasmid pPI-hRluc was generated from the plasmid pFKI341 PI-Luc/NS3-3'/ET, which encodes a genotype 1b (Con-1 strain) subgenomic replicon and was obtained from ReBLikon {11239}. The hRluc gene was PCR amplified from pF9 CMV hRluc-neo Flexi(R) (Promega, Madison, Wis.) by PCR using Accuprime Super Mix I (Invitrogen, Carlsbad, Calif.) and the primers PV_Rluc_Top and 3'-Rluc(NotI). These two primers have the following sequences and carry restriction sites for subsequent cloning: PV_Rluc_Top: 5' ATC AGA CAA TTG TAT CAT AAT GGC TTC CAA GGT GTA CG 3'; 3'-Rluc(NotI): 5' ACG TCA CTA TCT ACG CGG CCG CTT ACT GCT CGT TCT TC3' (NotI site underlined). The T7 Promoter, 5'UTR and Polio Virus IRES were PCR amplified from the plasmid pFKI341 PI-Luc/NS3-3'/ET using the primers 5'-P7(SbfI) and PV_Rluc_Bottom. These two primers have the following sequences and carry restriction sites for subsequent cloning: 5'-P7(SbfI): 5' CAA GCT AAG CTG CCT GCA GG T 3' (SbfI site underlined); PV_Rluc_Bottom: 5' CGT ACA CCT TGG AAG CCA TTA TGA TAC AAT TGT CTG AT. The subsequent PCR fragments from the two above reactions were then joined together using overlapping PCR and the primers 5'-P7(SbfI) and 3'-Rluc(NotI). The completed P7-5'UTR-Polio Virus IRES-hRluc amplification product was subcloned into pCR2.1-TOPO. The resulting plasmid was digested with SbfI and NotI, and the excised fragment (P7-5'UTR-Polio Virus IRES-hRluc) were ligated using T4 DNA ligase into pFKI341 PI-Luc/NS3-3'/ET digested with the same enzymes. The resulting vector, pPI-hRluc, was sequenced to confirm the correct orientation and sequence of the P75'UTR-Polio Virus IRES-hRluc region of the plasmid. The NS5B M423T mutation was introduced into a plasmid encoding the PI-hRluc replicon using a QuikChange II XL mutagenesis kit, following the manufacturer's instructions (Stratagene, La Jolla, Calif.). The mutation was confirmed by DNA sequencing. Replicon RNAs were transcribed in vitro from the replicon-encoding plasmid using a MEGAscript kit (Ambion, Austin, Tex.). RNA was transfected into Huh-lunet cells using the method of Lohmann et al. Briefly, cells were trypsinized and washed twice with PBS. A suspension of 4 $10^6$ cells in 400 μL of PBS were mixed with 5 μg of RNA and subjected to electroporation using settings of 960 μF and 270 V. Cells were transferred into 40 mL of pre-warmed culture medium and then seeded into 96-well plates (100 μL/well). Compounds were 3-fold serially diluted in 100% DMSO and added to cells at a 1:200 dilution, achieving a final DMSO concentration of 0.5% in a total volume of 200 μL/well. Cells were treated for three days after which culture media were removed, cells were lysed, and *Renilla luciferase* activity was quantified using a commercially available assay (Promega) and a Top Count instrument (Perkin Elmer, Waltham, Mass.).

Data Analysis.

Data were converted into percentages relative to untreated controls (defined as 100%), and $EC_{50}$ values were calculated by non-linear regression of two replicate data sets using XLfit 4 software (IDBS, Emeryville, Calif.). Resistance fold changes were calculated as the ratio of mutant to wild-type replicon $EC_{50}$. Results are shown in Table 2.

TABLE 2

| | Replicon transient transfection $EC_{50}$ (nM) | | |
| --- | --- | --- | --- |
| Example | wild-type | M423T | Fold shift |
| 3 | 5 | 14 | 2.7 |
| 6 | 8 | 40 | 5.2 |
| Comparative example 1 | 26 | 293 | 12 |
| Comparative example 2 | 10 | 343 | 35 |

Binding Affinity Measurements

As will be appreciated, direct measurements of binding affinity provide a sensitive method for determining the interaction of a small molecule drug with the binding pockets of closely-related proteins, and hence the effects of subtle structural modifications on comparative inhibitory effects. The methods described below and the results listed in Table 3 demonstrate that the compounds of this invention not only display similar or enhanced binding affinities to wild-type NS5B, but that the presence of unsaturation in the cyclohexenyl ring of Formula I in combination with an added methyl substituent confers surprising retention of binding affinity against the M423T mutant, which is generated in the clinic upon treatment of chronically-infected HCV patients with earlier NS5B thumb site II inhibitors (Wagner, F., Thompson, R. et al., Antiviral Activity of the Hepatitis C Virus Polymerase Inhibitor Filibuvir in Genotype 1 Infected Patients, Hepatology, 2011; Jiang, M., Ardzinski, A. et al, Characterization of HCV variants selected in genotype 1 patients who received 3 day monotherapy with VX-222, a non-nucleoside polymerase inhibitor, 17th international meeting on hepatitis C virus and related viruses, September 2010, Yokohama, Japan). Compounds with minimal fold difference in binding affinity may have particular clinical utility.

In vitro studies with NS5B employed soluble, 21 residue C-terminal truncated forms of the NS5b protein (amino acids 1-570; GT-1b; wild-type and mutant M423T. See Hung, M., Wang, R., Liu, X.: 'Preparation of HCV NS3 and NS5B to support small molecule drug discovery', Current Protocols in Pharmacology, 2011, in press). Surface Plasmon Resonance (SPR) was used to measure the binding affinity of compounds described herein to the protein constructs. Standard amine coupling was employed to link the protein to the surface of a Biacore CM5 sensor chip using 10 mM sodium acetate pH 5.5 buffer to an immobilization level of ~2500 RU. Experiments were performed using a Biacore T100 system at 25° C. in running buffer (50 mM Hepes pH 7.5, 5 mM $MgCl_2$, mM KCl, 1 mM EDTA, 1 mM TCEP, 0.01% P20, 5% DMSO). Compounds were tested in a 3-fold concentration dilution series for 8 concentrations starting at 162 nM, using an association phase of 60 seconds and dissociation phase of 5 minutes at a flow rate of 100 µl $min^{-1}$. At the end of each binding cycle, a 3-second injection of a buffer (10 mM disodium tetraborate, 1M NaCl, pH8.5) at 40 µl $min^{-1}$ was used as a regeneration step to remove compounds still bound to the NS5B surface. Response data were processed using the following procedure: injections aligned in X and Y directions, double referenced using both a reference surface and buffer injections, and DMSO correction for excluded volume effects. Processed data were analyzed using non-linear least squares analysis with a global fit of a 1:1 binding model with mass transport. Results are summarized in Table 3.

TABLE 3

| Example | Structure | Wild-type $K_D$ (nM) | M423T $K_D$ (nM) | Fold difference |
|---|---|---|---|---|
| 4 | 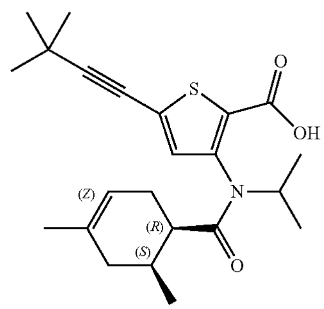 | 6.5 | 18.5 | 2.9 |
| 1 | 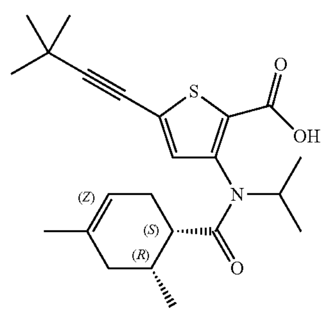 | 1.4 | 7.7 | 5.6 |
| 3 | 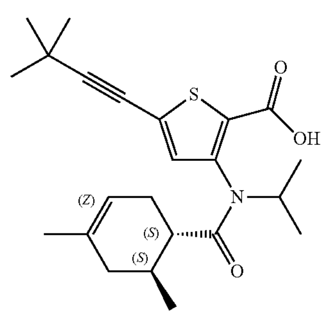 | 0.7 | 4.2 | 6.0 |
| 5 | 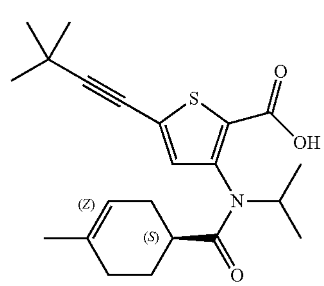 | 1.5 | 13.7 | 9.0 |

TABLE 3-continued

| Example | Structure | Wild-type $K_D$ (nM) | M423T $K_D$ (nM) | Fold difference |
|---------|-----------|----------------------|-------------------|-----------------|
| 2 | 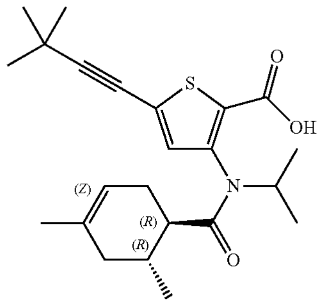 | 2.8 | 26.8 | 9.5 |
| 6 | 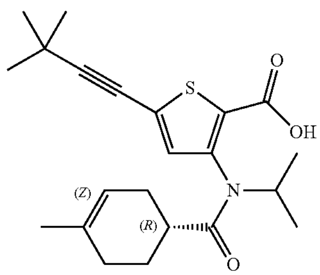 | 1.3 | 14.3 | 11 |
| Comparative example 1 | 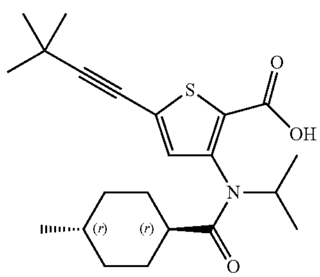 | 1.7 | 2.78 | 16 |
| Comparative example 4 | 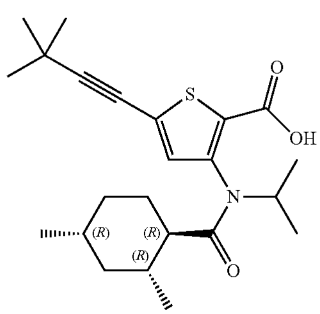 | 3.6 | 144.1 | 40 |

The specific pharmacological responses observed may vary according to and depending on the particular active compound selected or whether there are present pharmaceutical carriers, as well as the type of formulation and mode of administration employed, and such expected variations or differences in the results are contemplated in accordance with practice of the present invention.

Although specific embodiments of the present invention are herein illustrated and described in detail, the invention is not limited thereto. The above detailed descriptions are provided as exemplary of the present invention and should not be construed as constituting any limitation of the invention. Modifications will be obvious to those skilled in the art, and all modifications that do not depart from the spirit of the invention are intended to be included within the scope of the appended claims.

What is claimed is:

1. A compound of Formula I:

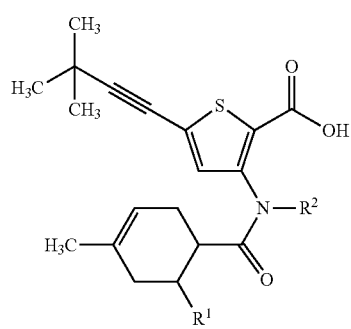

(I)

SEQUENCE LISTING

```
<160> NUMBER OF SEQ ID NOS: 4

<210> SEQ ID NO 1
<211> LENGTH: 38
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
atcagacaat tgtatcataa tggcttccaa ggtgtacg                              38

<210> SEQ ID NO 2
<211> LENGTH: 38
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
acgtcactat ctacgcggcc gcttactgct cgttcttc                              38

<210> SEQ ID NO 3
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
caagctaagc tgcctgcagg t                                                21

<210> SEQ ID NO 4
<211> LENGTH: 38
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
cgtcaccctt ggaagccatt atgatacaat tgtctgat                              38
``` or a pharmaceutically acceptable salt or ester thereof, wherein:

R¹ is H or methyl; and
R² is (C₁-C₆)alkyl;
wherein each alkyl represents a straight or branched chain.

2. The compound of claim 1 wherein the compound of formula (I) is a compound of formula (Ia) or I(b)

3. The compound of claim 1 wherein the compound of formula (I) is a compound selected from formula (Ic)-(If):

4. The compound of claim 1 wherein R¹ is H.
5. The compound of claim 1 wherein R¹ is methyl.
6. The compound of claim 3 which is a compound of formula (Ic):

or a pharmaceutically acceptable salt or ester thereof.

7. The compound of claim 1 wherein R² is isopropyl.
8. The compound of claim 1, selected from the group consisting of:

-continued

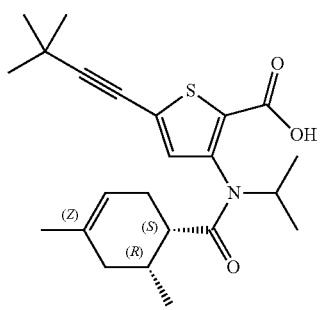

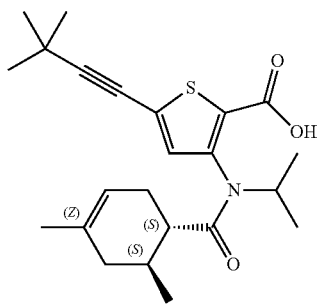

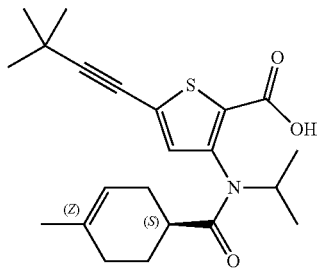

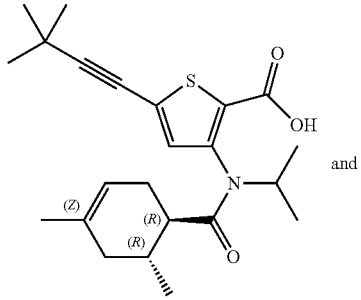 and

-continued

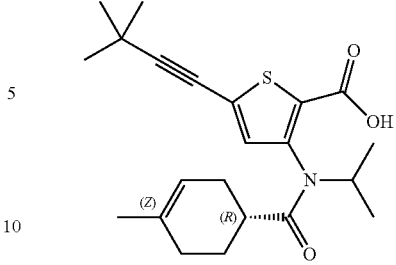

and pharmaceutically acceptable salts and esters thereof.

9. The compound of claim 1 selected from:

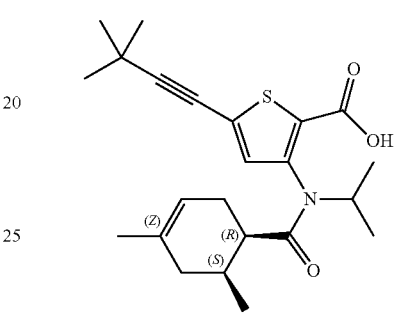

and pharmaceutically acceptable salts and esters thereof.

10. A pharmaceutical composition comprising a therapeutically effective amount of a compound of claim 1 and a pharmaceutically acceptable carrier or excipient.

11. The pharmaceutical composition of claim 10 further comprising at least one additional therapeutic agent selected from the group consisting of an interferon, ribavirin or an analog thereof, an HCV NS3 protease inhibitor, an NS5A inhibitor, an alpha-glucosidase 1 inhibitor, a hepatoprotectant, a mevalonate decarboxylase antagonist, an antagonist of the renin-angiotensin system, an endothelin antagonist, other anti-fibrotic agents, a nucleoside or nucleotide inhibitor of HCV NS5B polymerase, a non-nucleoside inhibitor of HCV NS5B polymerase, an HCV NS4B inhibitor, an inhibitor of viral entry and/or assembly, an TLR-7 agonist, cyclophilin inhibitor, an HCV IRES inhibitor, a pharmacokinetic enhancer and other drugs for treating HCV; or a mixture thereof.

* * * * *